(12) United States Patent
Dube et al.

(10) Patent No.: US 11,426,553 B2
(45) Date of Patent: Aug. 30, 2022

(54) PORTABLE GAS DELIVERY SYSTEM

(71) Applicant: Aeronics, Inc., Pittsburgh, PA (US)

(72) Inventors: Blake W. Dube, Pittsburgh, PA (US);
Mark B. Spitz, Pittsburgh, PA (US);
Benjamin K. Matzke, Pittsburgh, PA (US); Robert M. Miller, Denver, CO (US)

(73) Assignee: Aeronics, Inc., Pittsburgh, PA (US)

(*) Notice: Subject to any disclaimer, the term of this patent is extended or adjusted under 35 U.S.C. 154(b) by 687 days.

(21) Appl. No.: 16/386,055

(22) Filed: Apr. 16, 2019

(65) Prior Publication Data

US 2019/0314595 A1 Oct. 17, 2019

Related U.S. Application Data

(60) Provisional application No. 62/719,328, filed on Aug. 17, 2018, provisional application No. 62/658,214, filed on Apr. 16, 2018.

(51) Int. Cl.
*A61M 16/10* (2006.01)
*A61M 16/06* (2006.01)
*A61M 16/20* (2006.01)

(52) U.S. Cl.
CPC ........ *A61M 16/1005* (2014.02); *A61M 16/06* (2013.01); *A61M 16/105* (2013.01); *A61M 16/20* (2013.01); *A61M 2250/00* (2013.01)

(58) Field of Classification Search
CPC .............. A61M 16/1005; A61M 16/06; A61M 16/105; A61M 16/20; A61M 16/0875; A61M 16/022; A61M 16/201; A61M 39/1011; A61M 39/10; A61M 39/0677; B65D 25/38; A62B 7/02; F16L 29/02; F16L 37/24
USPC ......................................... 141/382, 381, 384
See application file for complete search history.

(56) References Cited

U.S. PATENT DOCUMENTS

| | | |
|---|---|---|
| D209,364 S | 11/1967 | Katzman |
| D210,435 S | 3/1968 | Boldt |
| D222,800 S | 1/1972 | Donoghue |
| D258,535 S | 6/1981 | Reichl |
| 4,274,404 A * | 6/1981 | Molzan ............... A62B 7/04 128/205.24 |
| 4,409,978 A * | 10/1983 | Bartos ............. C04B 41/009 128/205.12 |
| D279,312 S | 6/1985 | Pohlman |
| 4,928,859 A * | 5/1990 | Krahn ............. F16L 37/0841 285/317 |
| 4,955,372 A | 9/1990 | Blackmer et al. |

(Continued)

FOREIGN PATENT DOCUMENTS

| | | |
|---|---|---|
| CN | 206964906 | 2/2018 |
| KR | 300526519 | 4/2009 |

(Continued)

*Primary Examiner* — Samchuan C Yao
*Assistant Examiner* — Nathan M Le
(74) *Attorney, Agent, or Firm* — Dentons Cohen & Grigsby P.C.

(57) ABSTRACT

A portable gas delivery system 10 may generally comprise a gas container 20, a regulator 30, an adapter 40 to couple the regulator 30 to the container 20, and a tube or cannula 50 and/or a mask 60 fluidly connected to the container 20. Methods of making and using the portable gas delivery system are also described.

15 Claims, 26 Drawing Sheets

(56) References Cited

U.S. PATENT DOCUMENTS

| | | | |
|---|---|---|---|
| D356,153 S | 3/1995 | Peterhans | |
| 6,155,258 A | 12/2000 | Voege | |
| D466,208 S | 11/2002 | Emanuel | |
| 6,494,201 B1 | 12/2002 | Welik | |
| 6,739,578 B2* | 5/2004 | Barton | F16K 1/303 439/20 |
| 7,204,246 B1 | 4/2007 | Berinato | |
| 7,237,570 B2* | 7/2007 | Gamard | G05D 7/0133 137/614.19 |
| D561,331 S | 2/2008 | Benzick et al. | |
| 7,341,056 B1 | 3/2008 | Tucker | |
| D566,713 S | 4/2008 | Ah | |
| D610,250 S | 2/2010 | Neuner | |
| 7,832,395 B2 | 11/2010 | Rogers | |
| 8,960,727 B2* | 2/2015 | Kendrick | F16L 37/08 285/93 |
| 8,985,113 B2 | 3/2015 | Aldana | |
| D741,025 S | 10/2015 | Ross | |
| D773,035 S | 11/2016 | Neuner | |
| 2001/0020470 A1* | 9/2001 | Zupan | F16K 15/18 128/200.24 |
| 2002/0023649 A1* | 2/2002 | Gunaratnam | A61M 16/20 128/205.25 |
| 2002/0050275 A1* | 5/2002 | Koch | F17C 13/002 128/204.18 |
| 2002/0170557 A1 | 11/2002 | Schmidt | |
| 2003/0029450 A1 | 2/2003 | Lee et al. | |
| 2003/0033930 A1 | 2/2003 | Tom et al. | |
| 2005/0081849 A1 | 4/2005 | Warren | |
| 2005/0192538 A1 | 9/2005 | Voege | |
| 2007/0107730 A1 | 5/2007 | Sundhar | |
| 2008/0041375 A1 | 2/2008 | Stratton | |
| 2008/0116228 A1 | 5/2008 | Anthony et al. | |
| 2009/0107582 A1 | 4/2009 | Sayage | |
| 2009/0166226 A1* | 7/2009 | Radford | F17C 13/04 251/144 |
| 2013/0199523 A1 | 8/2013 | Chen | |
| 2016/0050884 A1 | 2/2016 | Ross | |
| 2018/0339126 A1* | 11/2018 | Blanton | F16K 31/402 |
| 2020/0030643 A1* | 1/2020 | Griffiths | A62B 9/02 |

FOREIGN PATENT DOCUMENTS

| | | |
|---|---|---|
| WO | 2005054742 | 6/2005 |
| WO | 2008064293 | 5/2008 |
| WO | 2017198680 | 11/2017 |
| WO | 2018019717 | 2/2018 |

* cited by examiner

PORTABLE GAS DELIVERY SYSTEM

CROSS-REFERENCE TO RELATED APPLICATIONS

This application claims priority to U.S. Provisional Application Ser. No. 62/658,214, filed on Apr. 16, 2018, and U.S. Provisional Application Ser. No. 62/719,328, filed Aug. 17, 2018, each of which is hereby incorporated by reference in its entirety.

FIELD OF THE INVENTION

The present invention generally relates to gas delivery systems, and in particular, portable medical grade gas (e.g., oxygen) delivery systems as well as methods of making and using the same.

BACKGROUND

Oxygen is essential for normal cell metabolism in animals with lungs, such as humans and non-human animals. Air typically includes 21% oxygen by volume. This may be normally sufficient for respiration, but in some circumstances, the oxygen supply to cells may be compromised. In such circumstances, oxygen supplementation may be used to increase oxygen levels to the cells. Supplemental oxygen may be delivered via a nasal cannula or mask that is connected to a pressurized oxygen source, such as a conventional oxygen tank. Conventional pressurized oxygen sources may suffer from one or more of the following limitations: weights over 10 pounds making them difficult to transport and/or use, operate at a high compression pressure (500-2200 PSI or greater), lack a regulator to control the flow of gas from the container at low pressures and/or flowrates, have a regulator difficult to attach to the container by hand-tightening, have a regulator weighing more than 0.5 pounds, have a short shelf life, and/or need to be refilled when empty.

Accordingly, more efficient and/or cost-effective portable gas delivery systems and methods of making and using the same may be desirable.

SUMMARY

A portable gas delivery system may generally comprise a pressurized gas container having up to 1000 PSI pressurized gas, an internal liquid volume up to 1 L, an internal gas volume up to 40 L under pressure and room temperature, and a burst pressure less than 1000 PSI; a regulator in fluid communication with the container to provide the gas at an adjustable volumetric flow rate from 0-10 L/min and an inlet pressure up to 1000 PSI; and an adapter to removably couple and sealingly engage the regulator to the container, wherein the system has a total weight less than 5 pounds, and wherein the system is in an open position when the adapter is in a first position and the system is in a closed position when the adapter is in a second position.

A portable oxygen system to deliver medical grade oxygen to a patient may generally comprise a low pressure gas container comprising less than 250 PSI pressurized medical grade oxygen, an internal liquid volume up to 0.65 L, an internal oxygen gas volume up to 10 L under pressure and room temperature, and a burst pressure less than 450 PSI, a low pressure regulator in fluid communication with the gas container to provide the oxygen at an adjustable volumetric flow rate from up to 3.0 L/min and an inlet pressure up to 250 PSI; and a two-piece adapter comprising an inner portion removably coupled to and slidably engaged with an outer portion to control a flow of the oxygen between the container and the regulator, wherein the inner portion is threadingly engaged to an inlet of the regulator and the outer portion is snap fitted to the container; and a mask removably coupled to an outlet of the regulator to deliver the oxygen to the patient, and wherein the container has a weight less than 2 pounds, and wherein the system is in an open position when the inner portion of the adapter is in a first position relative to the outer portion and the system is in a closed position when the inner portion of the adapter is in a second position relative to the outer portion.

DESCRIPTION OF THE FIGURES

The invention described herein may be better understood by reference to the accompanying figures, in which.

Figure 1:
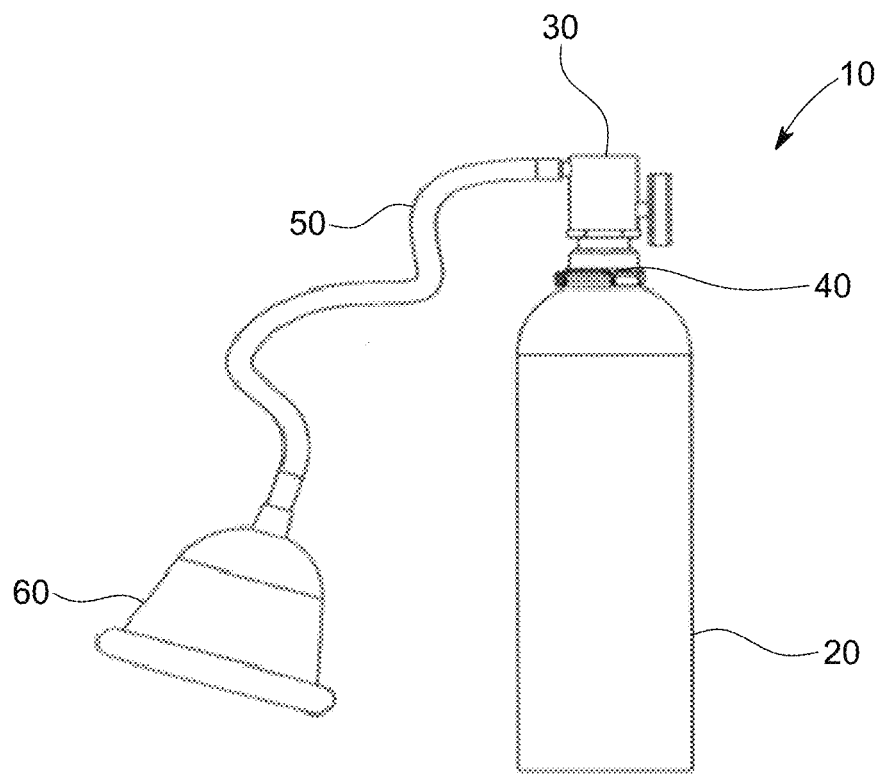
FIG. 1. illustrates a portable gas delivery system according to the present invention.
Figure 2:
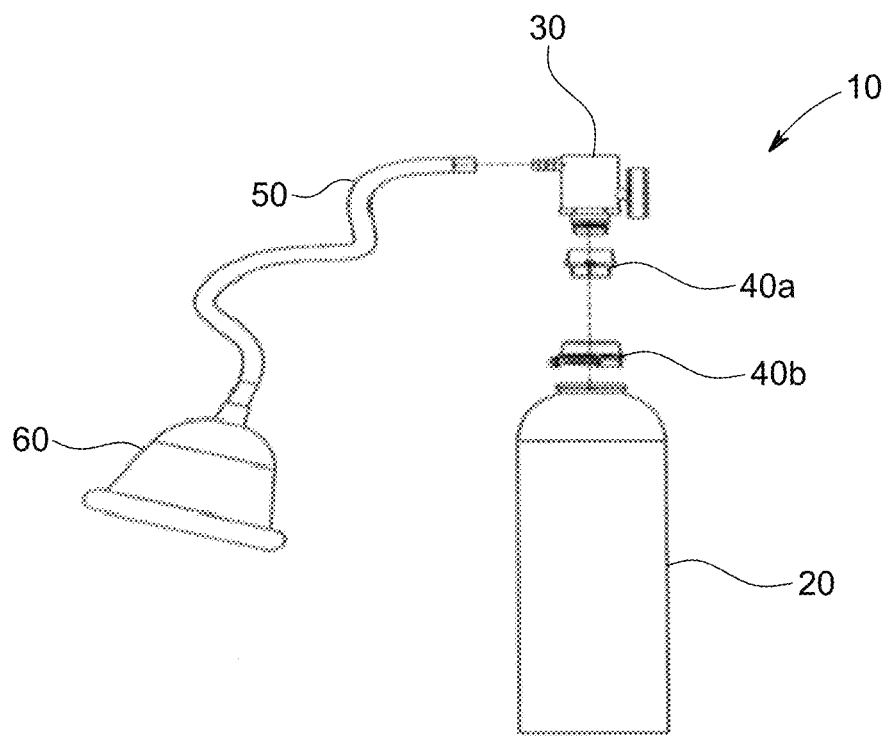
FIG. 2. illustrates an exploded view of the portable gas delivery system of FIG. 1.
Figure 3:
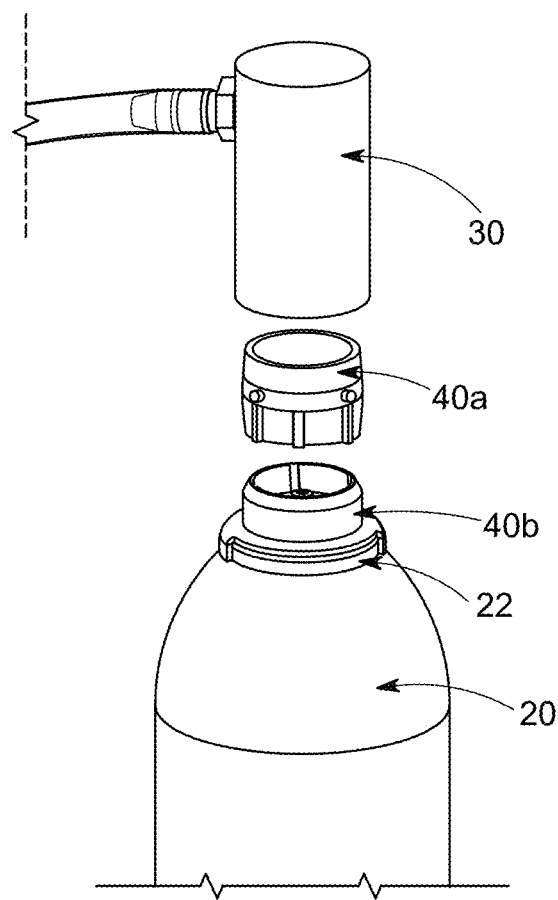
FIG. 3 illustrates a partially exploded view of the portable gas delivery system of FIG. 7.

Relative terms such as "lower" or "bottom" and "upper" or "top" may be used herein to describe one element's relationship to another element illustrated in the figures. It will be understood that relative terms are intended to encompass different orientations of aspects of the systems in addition to the orientation depicted in the figures. By way of example, if aspects of the invention shown in the drawings are turned over, elements described as being on the "bottom" side of the other elements would then be oriented on the "top" side of the other elements as shown in the relevant drawing. The term "bottom" may therefore encompass both an orientation of "bottom" and "top" depending on the particular orientation of the figures.

DETAILED DESCRIPTION

As generally used herein, the articles "one", "a", "an" and "the" refer to "at least one" or "one or more", unless otherwise indicated.

As generally used herein, the terms "including" and "having" mean "comprising".

As used herein, the terms "connected", "coupled", "attached", and/or "joined" are interchangeably used to indicate either a direct connection between two components or, where appropriate, an indirect connection to one another through intervening or intermediate components. In contrast, when a component is referred to as being "directly connected", "directly coupled", "directly attached", and/or "directly joined" to another component, there are no intervening components. When a component is referred to as being "integral" or "integrated" to another component, the components are permanently formed as a single unitary body with one another that is not removable in nature unless otherwise stated.

As generally used herein, the term "room temperature" refers to 20-25° C.

As generally used herein, the term "substantially," mean a deviation of no more than 20%, such as no more than 10%, and preferably no more than 5% from a given value.

As generally used herein, the term "about" refers to an acceptable degree of error for the quantity measured, given the nature or precision of the measurements. Typical exemplary degrees of error may be within 20%, 10%, or 5% of a given value or range of values. Alternatively, and particularly in biological systems, the terms "about" refers to values within an order of magnitude, potentially within 5-fold or 2-fold of a given value.

All numerical quantities stated herein are approximate unless stated otherwise. Accordingly, the term "about" may be inferred when not expressly stated. The numerical quantities disclosed herein are to be understood as not being strictly limited to the exact numerical values recited. Instead, unless stated otherwise, each numerical value is intended to mean both the recited value and a functionally equivalent range surrounding that value. At the very least, and not as an attempt to limit the application of the doctrine of equivalents to the scope of the claims, each numerical parameter should at least be construed in light of the number of reported significant digits and by applying ordinary rounding techniques. Notwithstanding the approximations of numerical quantities stated herein, the numerical quantities described in specific examples of actual measured values are reported as precisely as possible.

Any numerical range recited in this specification is intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this disclosure is intended to include all lower numerical limitations subsumed therein and any minimum numerical limitation recited in this disclosure is intended to include all higher numerical limitations subsumed therein. Accordingly, Applicants reserve the right to amend this specification, including the claims, to expressly recite any sub-range subsumed within the ranges expressly recited herein.

In the following description, certain details are set forth in order to provide a better understanding of various embodiments of portable oxygen systems. However, a person having ordinary skill in the art will understand that these embodiments may be practiced without these details and/or in the absence of any details not described herein. In other instances, well-known structures, methods, and/or techniques associated with methods of practicing the various embodiments may not be shown or described in detail to avoid unnecessarily obscuring descriptions of other details of the various embodiments.

This disclosure describes various features, aspects, and advantages of various embodiments of portable gas delivery systems. It is understood, however, that this disclosure embraces numerous alternative embodiments that may be accomplished by combining any of the various features, aspects, and advantages of the various embodiments described herein in any combination or sub-combination that one of ordinary skill in the art may find useful. Such combinations or sub-combinations are intended to be included within the scope of this specification. As such, the claims may be amended to recite any features or aspects expressly or inherently described in, or otherwise expressly or inherently supported by, the present disclosure. Further, Applicants reserve the right to amend the claims to affirmatively disclaim any features or aspects that may be present in the prior art. The various embodiments disclosed and described in this disclosure may comprise, consist of, or consist essentially of the features and aspects as variously described herein.

The present invention is generally directed to portable gas delivery systems as well as methods of making and using the same.

Without wishing to be bound to any particular theory, the present invention may provide one or more of the following advantages relative to conventional portable gas delivery systems: weigh less than 5 pounds, up to 2 pounds, up to 1.5 pounds, or up to 1 pound; operate at low pressure up to 500 PSI, up to 250 PSI, or up to 210 PSI; have a low pressure regulator to control the flow of gas from the container at low pressures less than 500 PSI, up to 250 PSI, or up to 210 PSI and/or flowrates less than 3 L/min, 2 L/min, 1 L/min or 0.5 L/min; have a container weighing less than 5 pounds, less than 2 pounds, or up to 0.5 pounds; have a regulator weighing less than 5 pounds, less than 2 pounds, or up to 0.5 pounds, have a regulator easier to attach to the container by hand-tightening; have a longer shelf life; and/or be single-use and/or disposable when empty; have an absorbent to increase the gas capacity by up to 10 times, such as 1.5-10 times, 1.5-5 times, 5-10 times, 2 times, 3 times, or 4 times relative to a conventional portable gas delivery system lacking the absorbent; an internal filter comprising a foam stabilizer to mitigate dust generation and/or adsorbent displacement by minimizing movement of the adsorbent in the container and/or filter the gas prior to delivery; an external filtering system to deliver purified oxygen with little or no particulate impurities from the adsorbent and allow the user to breathe oxygen that is free or substantially free of particulates and other impurities from the absorbent; and an ergonomic mask and/or lid including the filtering system to allow the user to access the stored oxygen in an intuitive manner.

The gas may comprise oxygen, nitrogen, nitrous oxide, carbon dioxide, hydrogen, helium, nitric oxide, argon, neon, krypton, acetylene, butane, propane, halocarbon gases (e.g., FREON), and/or medical grade gases, such as carbon dioxide, helium, medical air, nitrogen, nitrous oxide, and oxygen. Medical grade gases may have a purity of at least 99.0%, 99.5%, 99.9%, 99.95%, 99.99%, 99.995%, and 99.999%. In other words, medical grade gases may comprise impurities up to 1%, up to 0.5%, up to 0.1%, up to 0.05%, up to 0.01%, up to 0.005%, and up to 0.001%.

The portable gas delivery systems may be used to deliver gas to a user. The user may comprise one of a human and a non-human animal, such as livestock, zoo animals, equines, and pets such as dogs, cats, rabbits, ferrets, pigs, rodents, such as gerbils, hamsters, chinchillas, rats, and guinea pigs, avian pets, such as parrots, passerines, and fowl, reptile pets, such as turtles, alligators, crocodiles, lizards, and snakes, and arthropod pets, such as tarantulas and hermit crabs. The user may comprise a patient that may benefit from supplemental medical grade gases, such as oxygen.

Referring to FIGS. 1-9, a portable gas delivery system 10 may generally comprise a gas container 20, a regulator 30, an adapter 40 to couple the regulator 30 to the container 20, and a tube or cannula 50 and/or a mask 60 fluidly connected to the container 20. Each of the regulator 30, adapter 40, and cannula 50 and/or mask 60 may comprise a single unit or system or may be integrated to form a single unit or system. For example, the portable gas delivery system may comprise the regulator integral with the adapter, the adapter integral with the mask, the mask integral with the cannula, and combinations thereof. The container may comprise a single-use, non-refillable and/or disposable container designed and configured for one-time use and then disposed of, recycled, or destroyed, and/or not intended to be filled again with gas when partially or completely empty of gas. For example, the portable gas delivery system may lack a refill adapter to refill the container with gas after one-time use. The present invention may comprise a kit including at least one of the portable gas delivery systems and/or components thereof. The kit may comprise at least one gas container, a regulator, an adapter, and optionally, at least one of a tube or cannula and/or a mask. For example, the kit may comprise two or more of the gas containers, one regulator, one adapter, and one cannula and mask. The system may have a weight less than 10 pounds, less than 5 pounds, less than 2 pounds, or up to 1 pound.

The container may have a capacity to store up to 1 L of liquid gas and up to 40 L of gas under pressure at room temperature. The gas may be in a liquid or gaseous state or a mixture of liquid and gas depending upon the temperature and operating conditions. For example, the container may have a liquid gas volume of 0.25-1 L and a gas volume of 0.5-40 L of gas under pressure at room temperature. The container may have a liquid gas volume of 0.25 L, 0.5 L, 0.65 L, 0.75 L, 0.8 L, or 0.9 L and a gas volume of 0.5-10 L, 0.5-20 L, 10-20 L, or up to 30 L of gas under pressure at room temperature. The capacity of the container may provide a constant flow rate for a single-use at room temperature of up to 10 gaseous liters per minute for a duration up to 4 minutes. For example, the capacity of the container may provide a constant flow rate for single-use at room temperature of up to 3 gaseous liters per minute for a duration up to 13 minutes, 2.5 gaseous liters per minute for a duration up to 16 minutes, 2 gaseous liters per minute for a duration up to 20 minutes, 1 gaseous liters per minute for a duration up to 40 minutes and/or 0.5 gaseous liters per minute for a duration up to 80 minutes. The capacity of the container may provide a constant flow rate for single-use at room temperature of up to 3 gaseous liters per minute for a duration up to 3.3 minutes. For example, the capacity of the container may provide a constant flow rate for single-use at room temperature of up to 2 gaseous liters per minute for a duration up to 5 minutes, up to 1 gaseous liters per minute for a duration up to 10 minutes, and up to 0.5 gaseous liters per minute for a duration up to 20 minutes.

The container may have an internal pressure up to 1000 PSI. The container may comprise a low-pressure container having an internal pressure from greater than zero to 1000 PSI, up to 500 PSI, greater than zero to 500 PSI, up to 250 PSI, greater than zero to 250 PSI, up to 210 PSI, greater than zero to 210 PSI, up to 200 PSI, greater than zero to 200 PSI, up to 150 PSI, greater than zero to 150 PSI, up to 140 PSI, greater than zero to 140 PSI, up to 100 PSI, and/or greater than zero to 100 PSI. For example, the container may have an internal pressure greater than 140 PSIG but not exceeding 250 PSIG at 55° C., such as 200-240 PSIG and 210 PSIG at 55° C. The container may having a bursting pressure of at least 200 PSI, at least 240 PSI, at least 270, at least 350 PSI, at least 400 PSI, at least 450 PSI, at least 500 PSI, at least 1000 PSI, less than 5000 PSI, less than 2750 PSI, less than 1000 PSI, less than 500 PSI, 200-500 PSI, 240-500 PSI, 270500 PSI, 300-500 PSI, and/or 400-500 PSI. For example, the container may have a bursting pressure of 32 bar (464 PSI). In other words, the container may burst at a pressure of 32 bar but not burst at a pressure less than 32 bar. The burst pressure may be 1.5 times the operating pressure. The container may have a weight less than 10 pounds, less than 5 pounds, less than 2 pounds, less than 1 pound, or up to 0.5 pounds.

Figure 4:
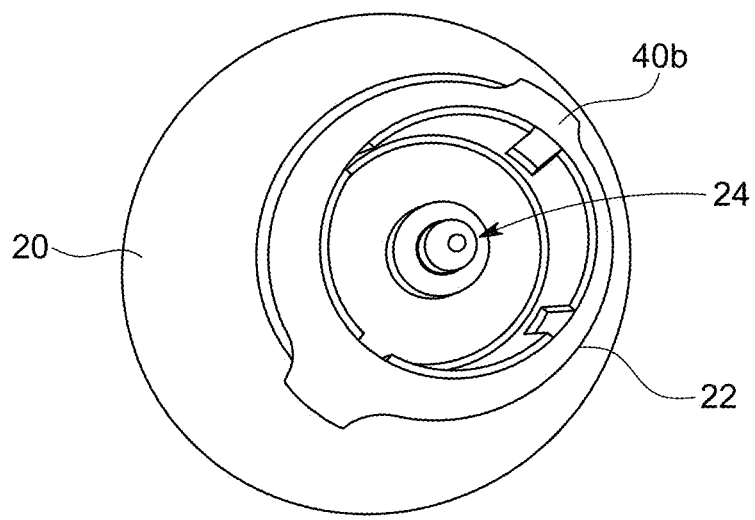
FIGS. 4 and 5 illustrate top and perspective views of the portable gas delivery system of FIG. 3.
Figure 5:
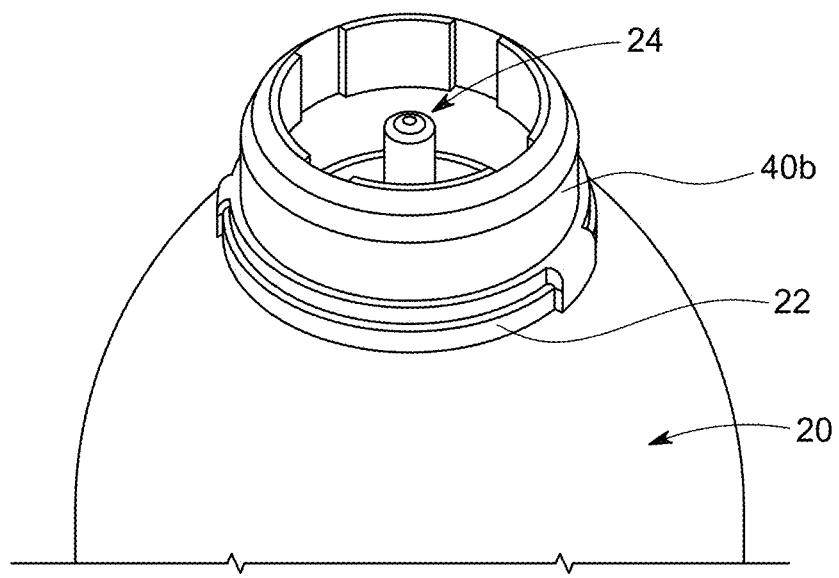
Figure 6:
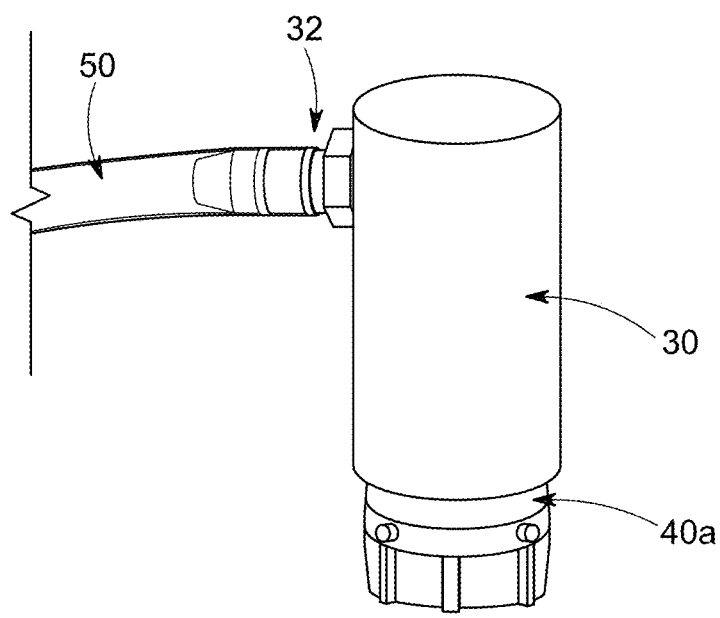
FIG. 6 illustrates a regulator coupled to an inner portion of an adapter of the portable gas delivery system of FIG. 3.
Figure 7:
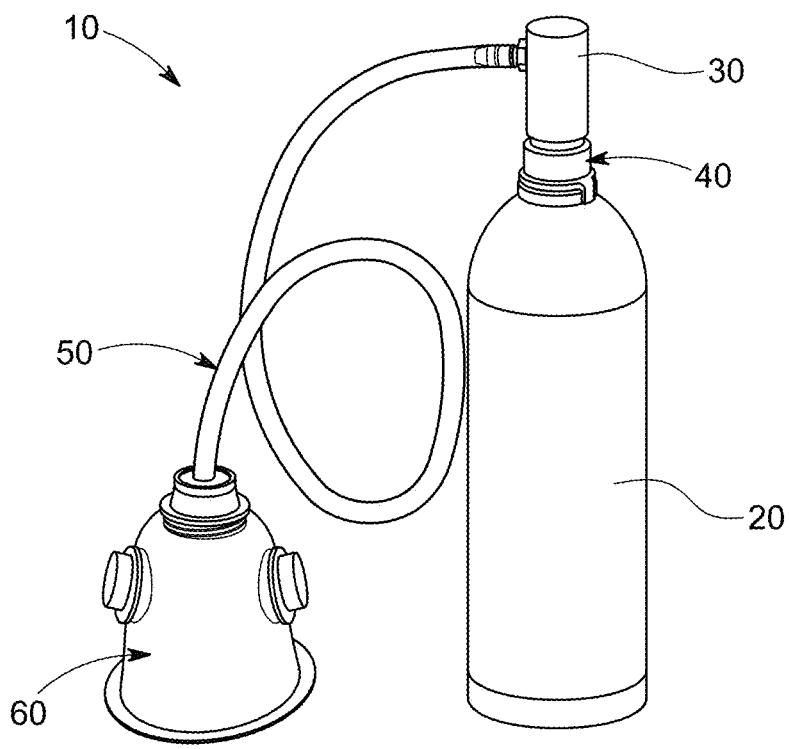
FIG. 7 illustrates a portable gas delivery system according to the present invention.
Figure 8:
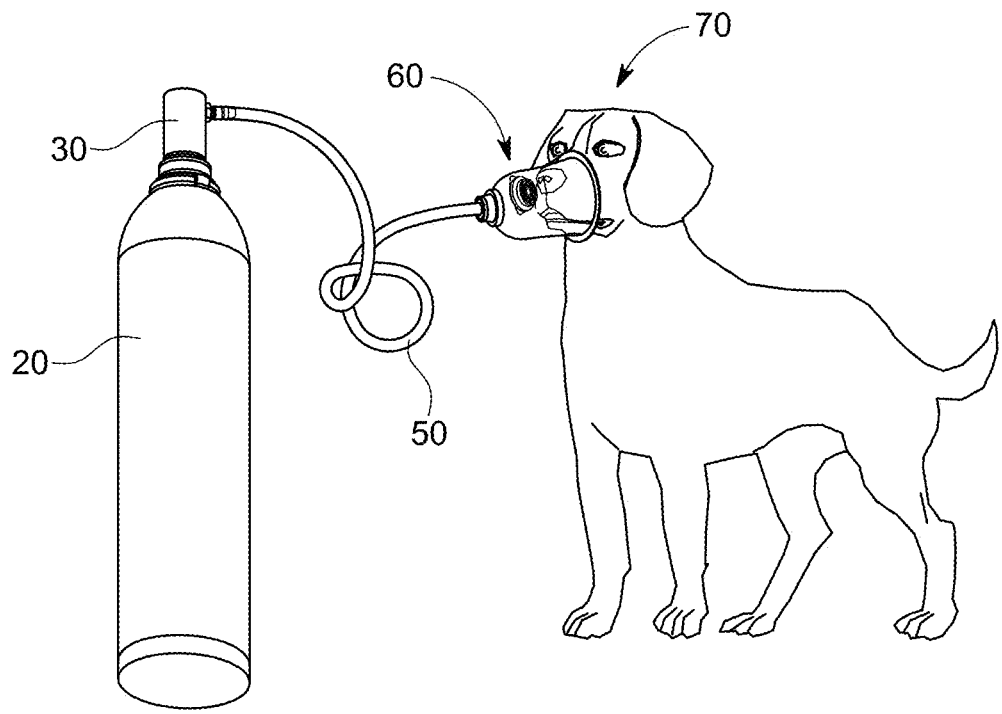
FIG. 8 illustrates the use of the portable gas delivery system of FIG. 7.
Figure 9:
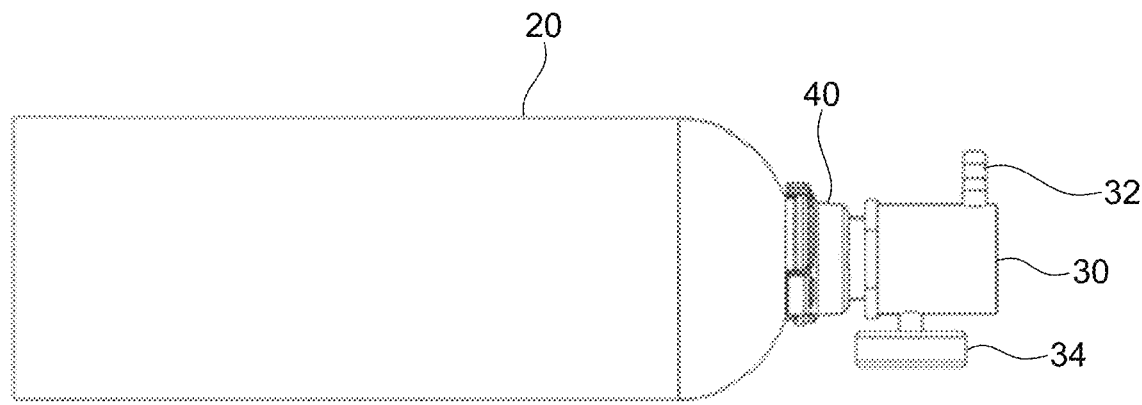
FIG. 9 illustrates a portable gas delivery system comprising a gas container, an adapter, and a regulator according to the present invention.
Figure 10:
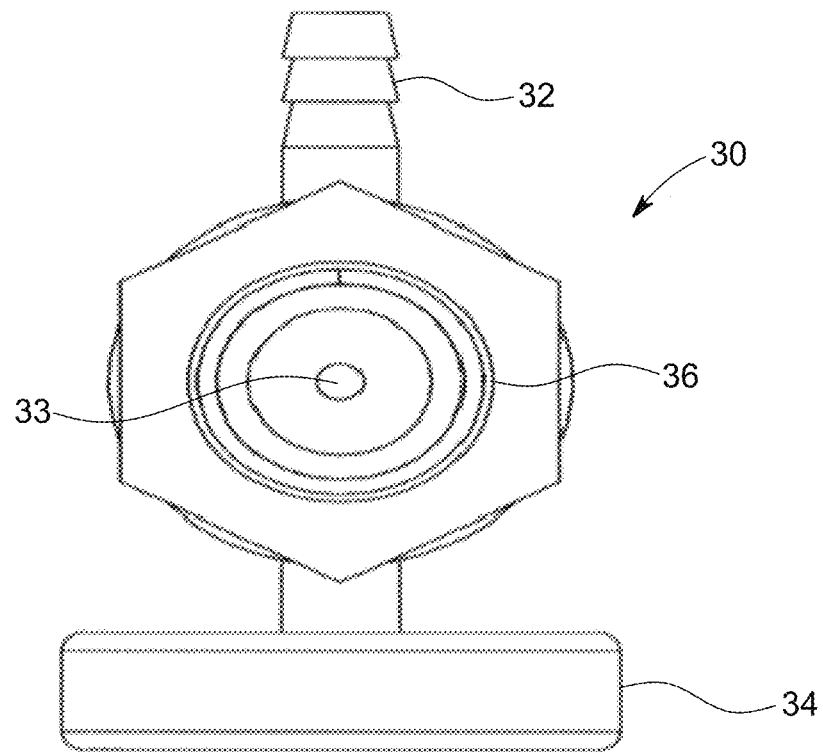
FIGS. 10-14 illustrate a regulator of the portable gas delivery system according to the present invention.
Figure 11:
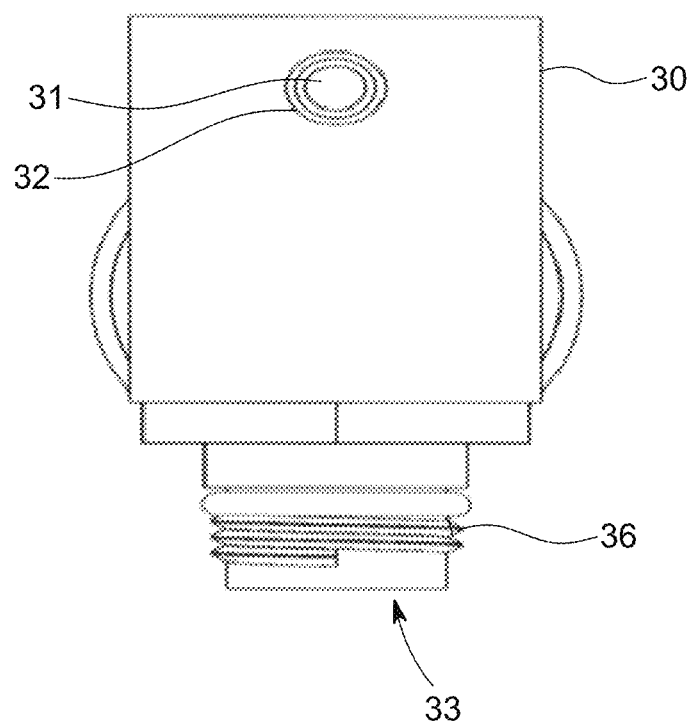
Figure 12:
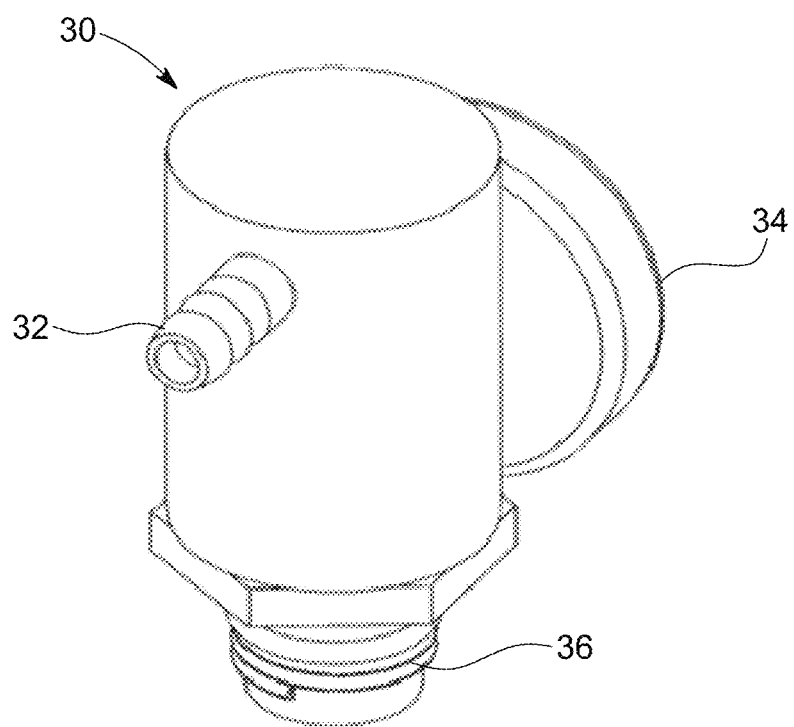
Figure 13:
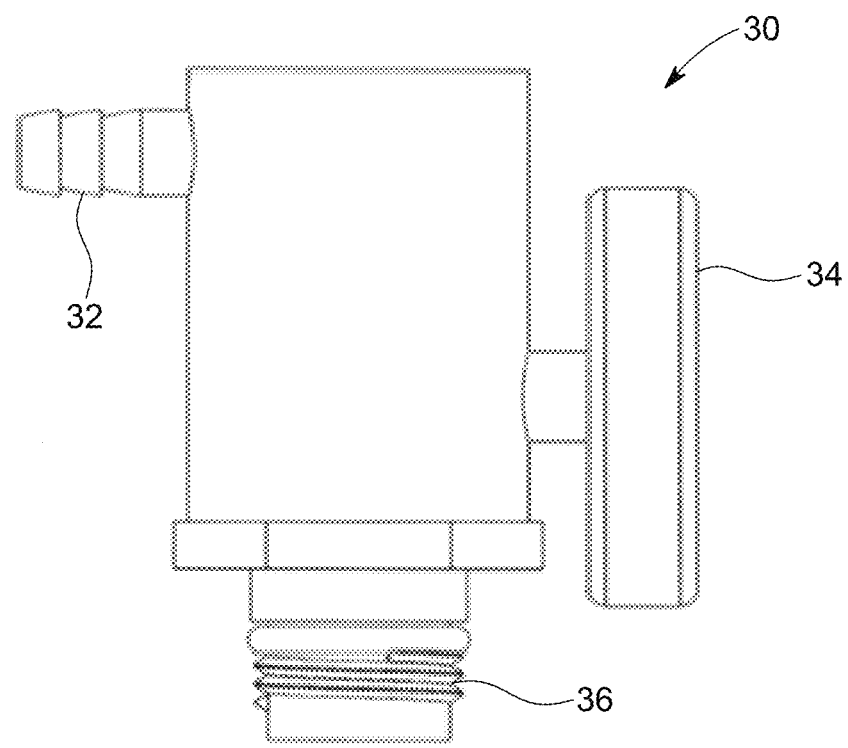
Figure 14:
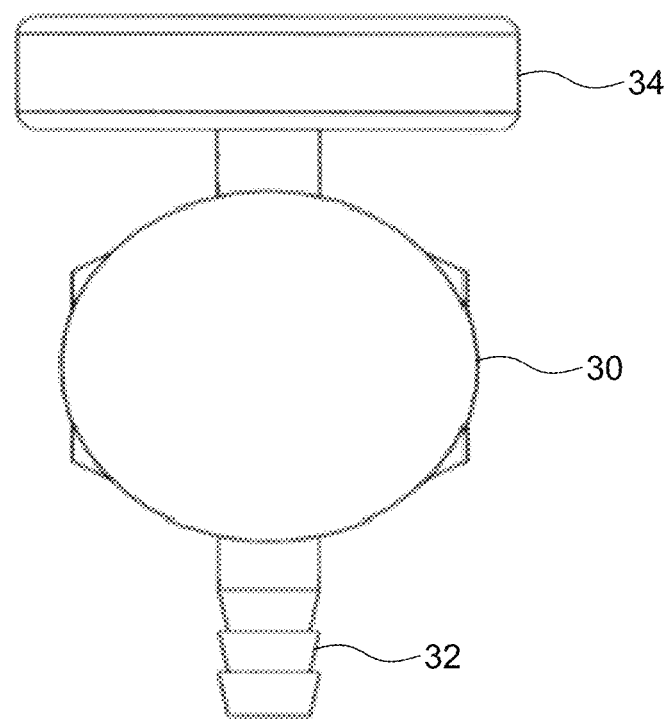
Figure 15:
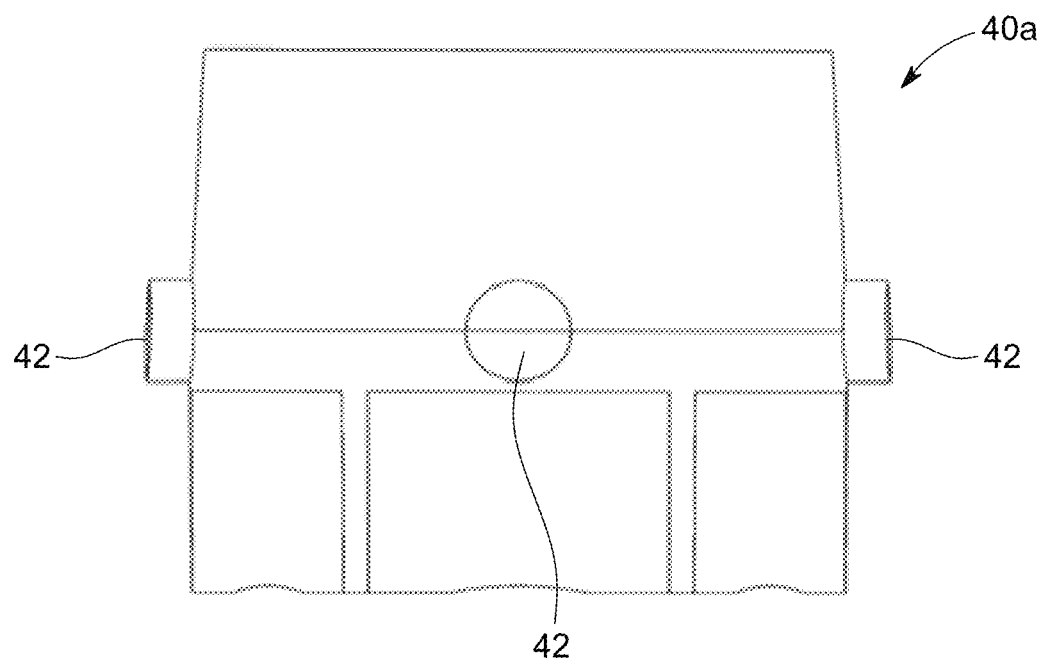
FIGS. 15-22 illustrate an adapter having three tabs of the portable gas delivery system according to the present invention.
Figure 16:
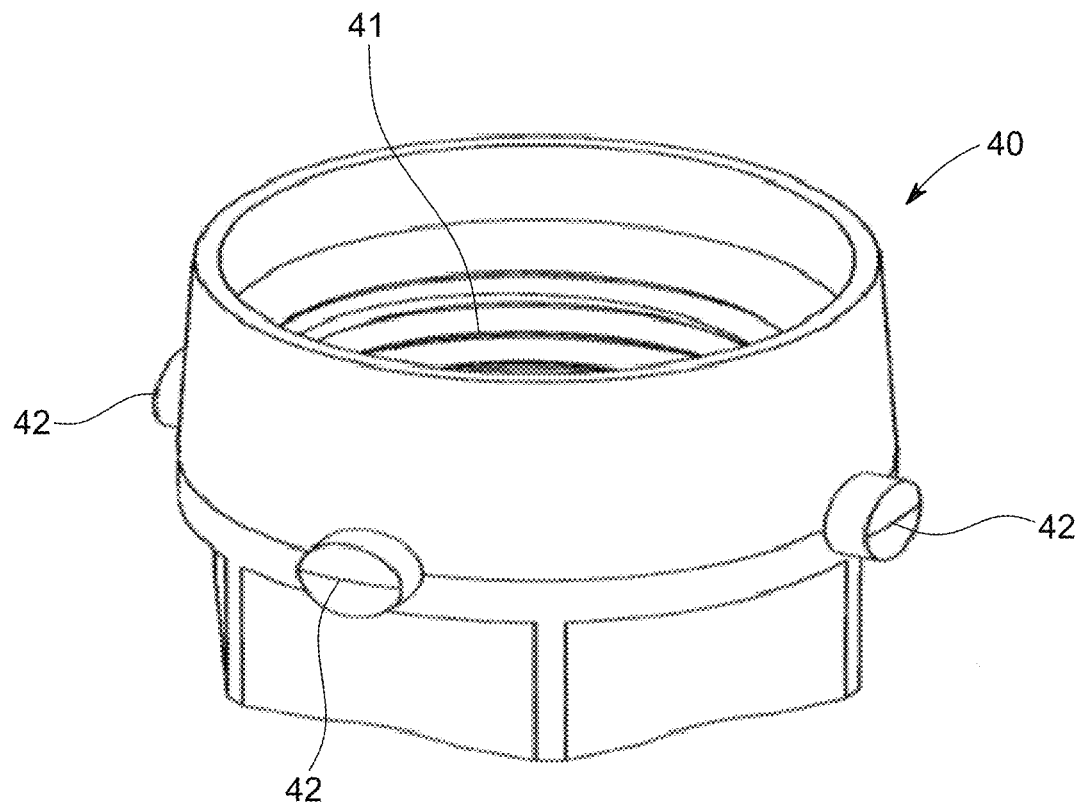
Figure 17:
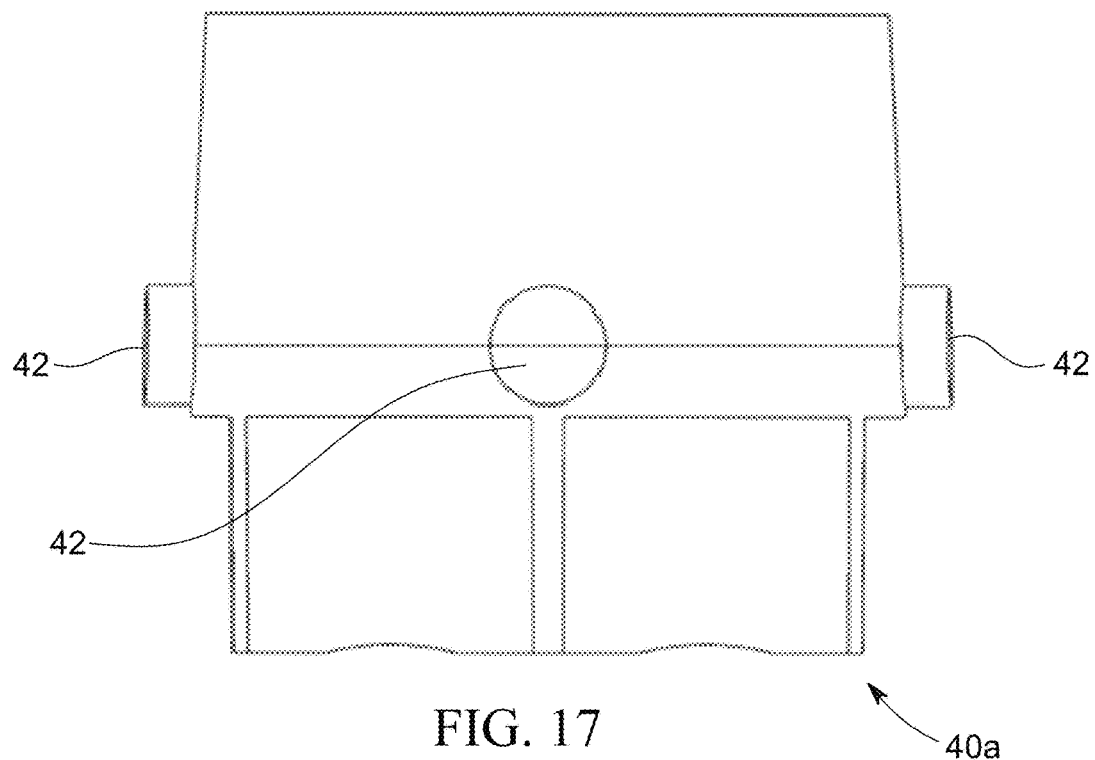
Figure 18:
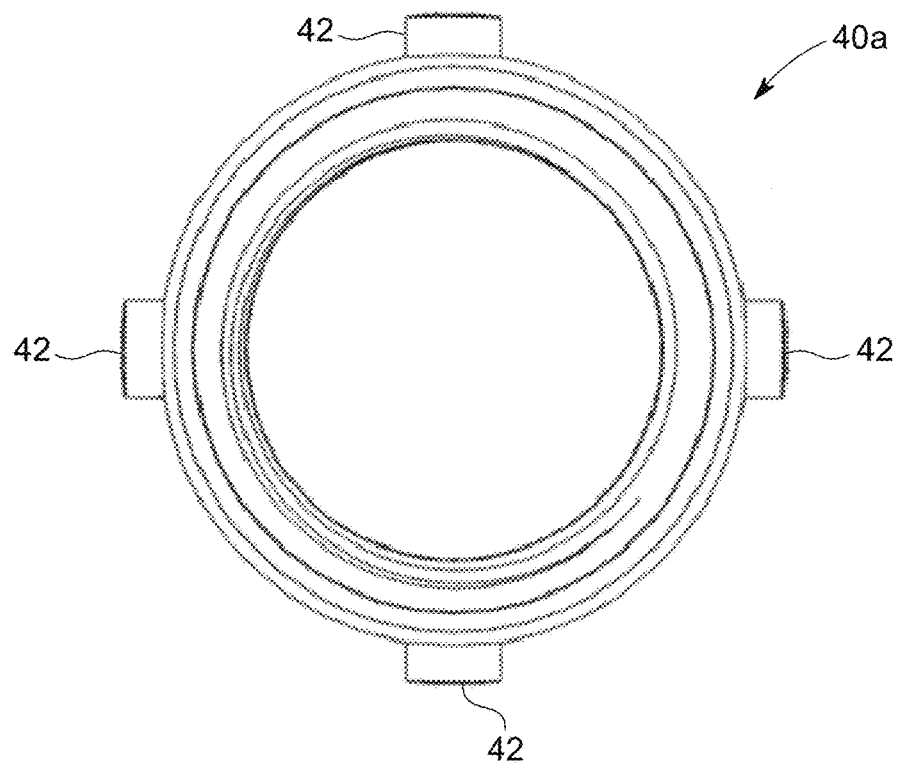
Figure 19:
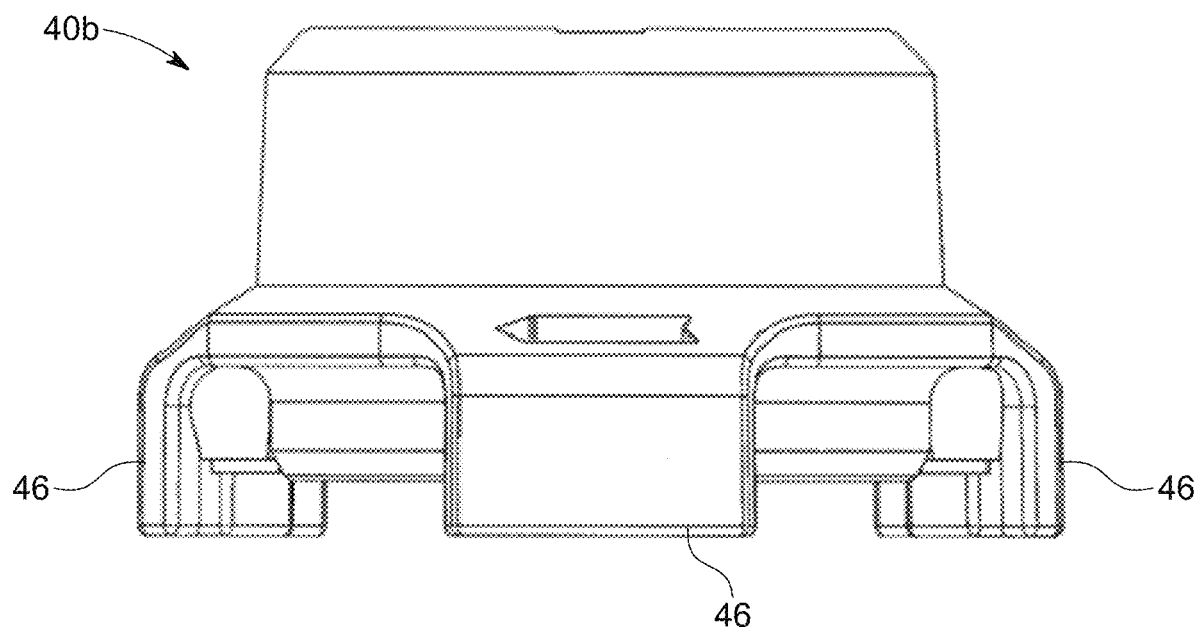
Figure 20:
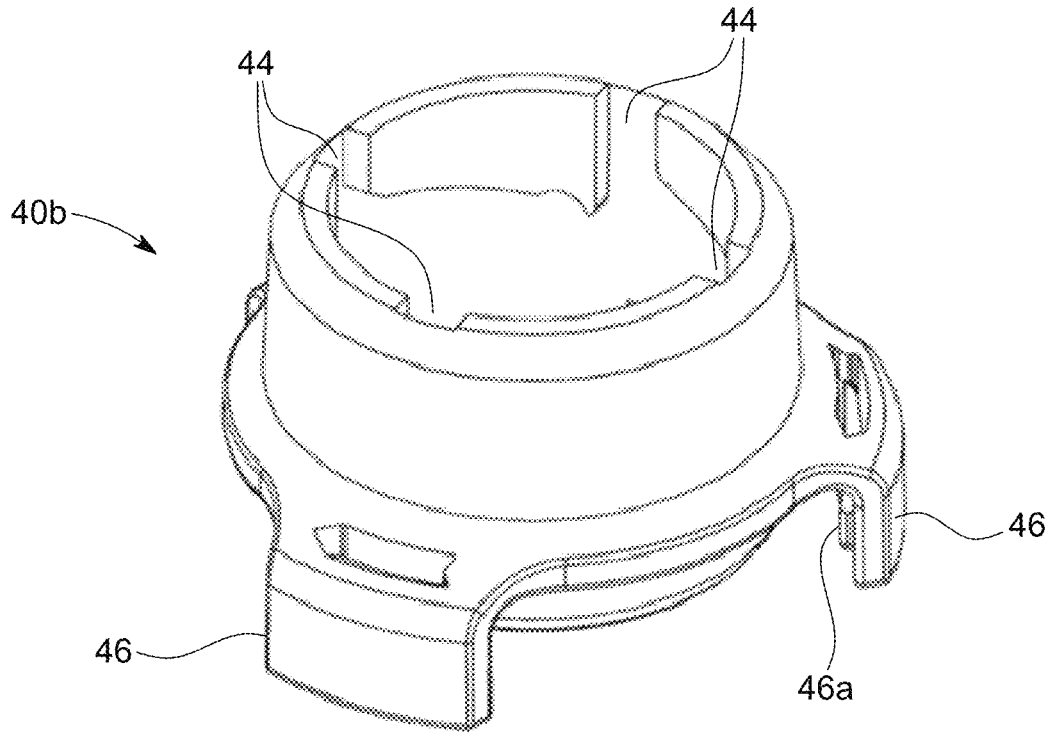
Figure 21:
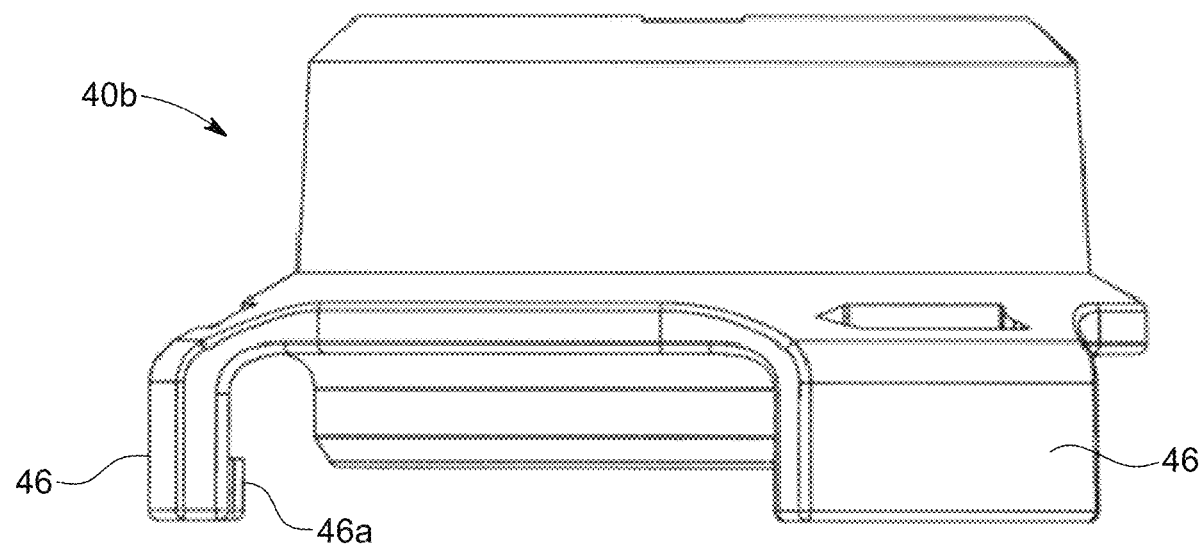
Figure 22:
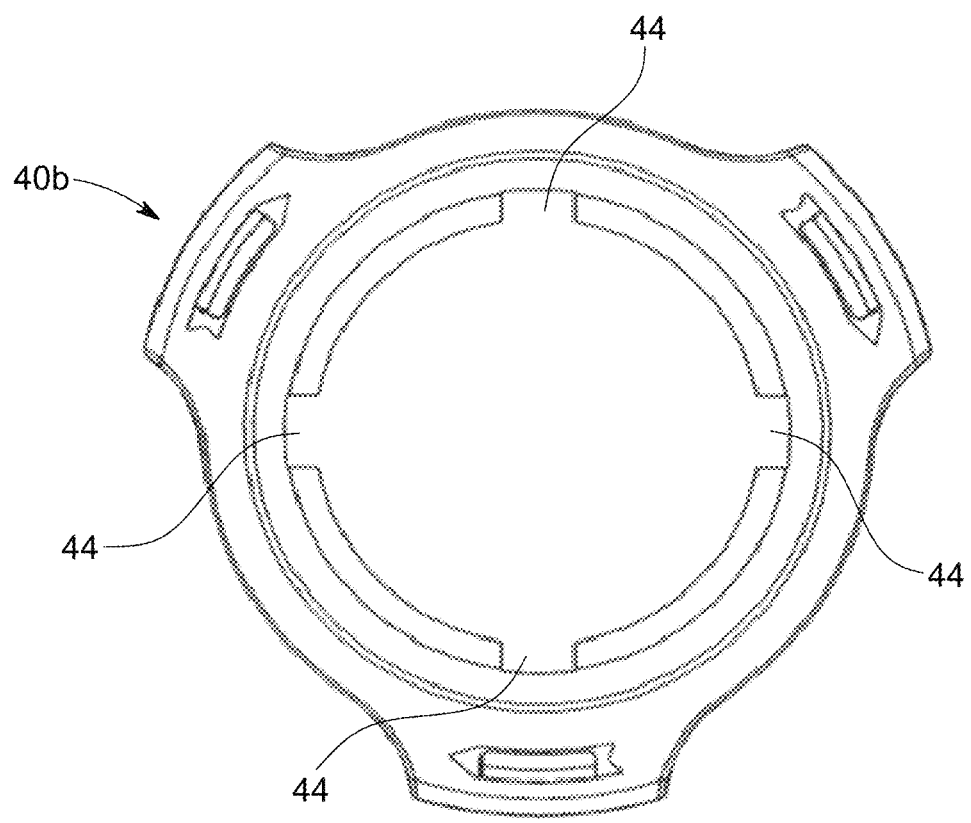
Figure 23:
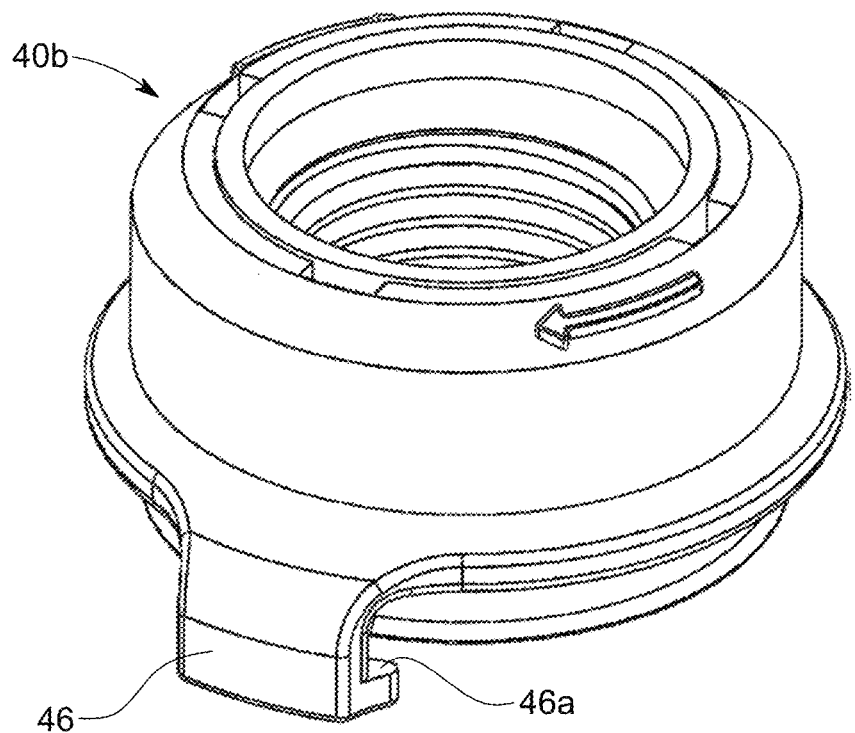
FIGS. 23-34 illustrate an adapter having two tabs of the portable gas delivery system according to the present invention.
Figure 24:
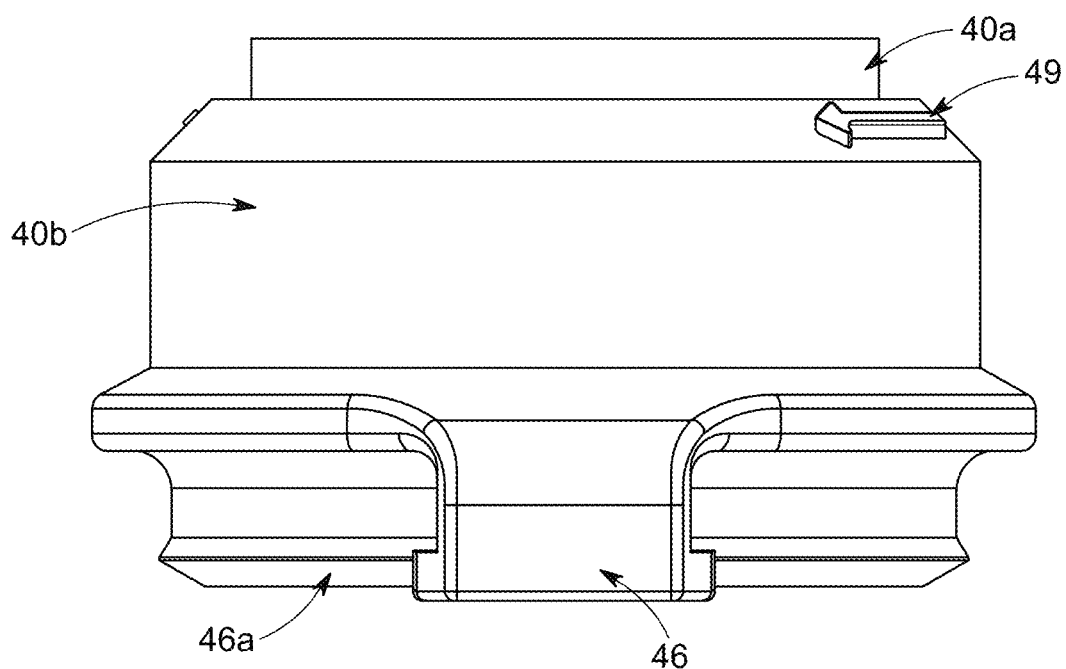
Figure 25:
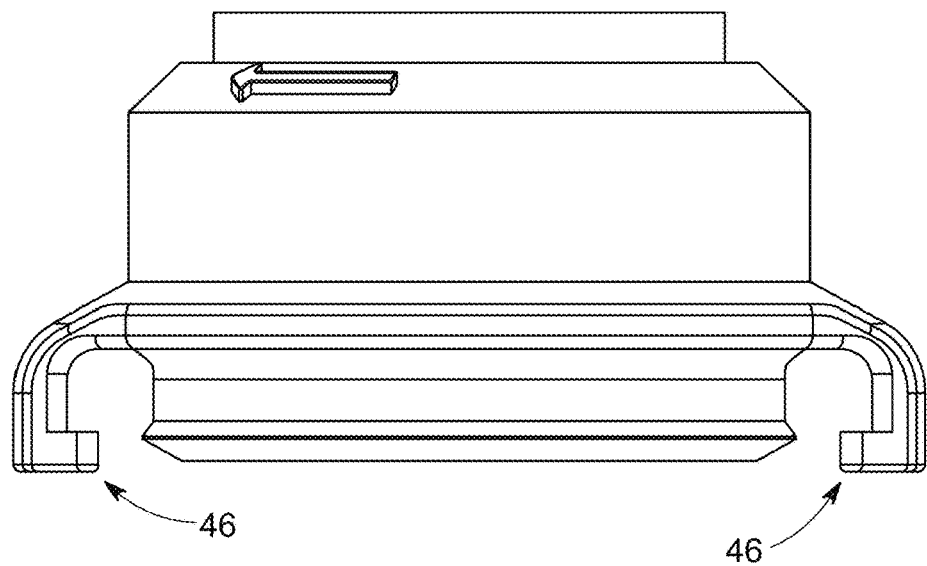
Figure 26:
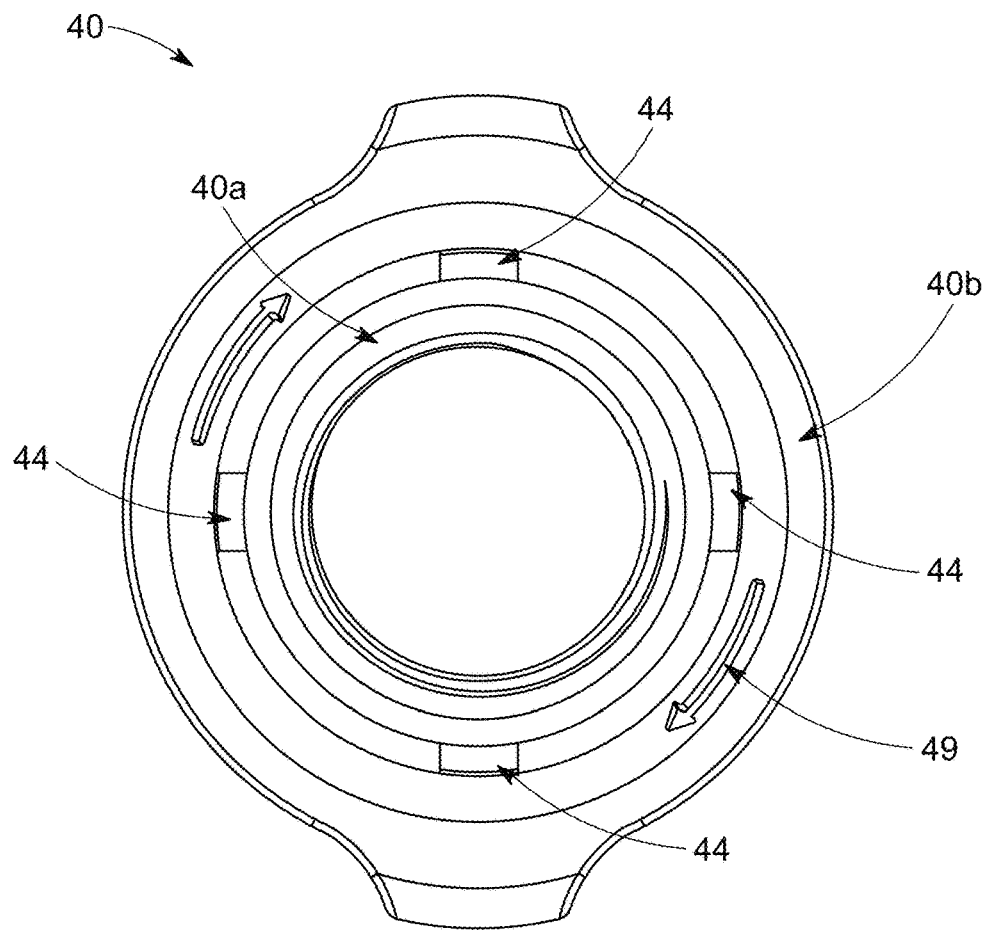
Figure 27:
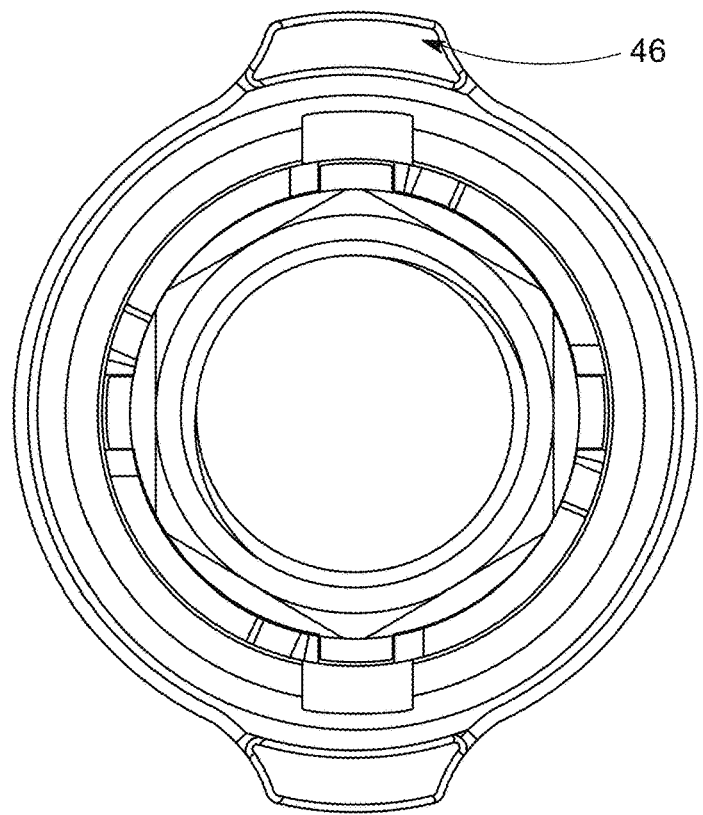
Figure 28:
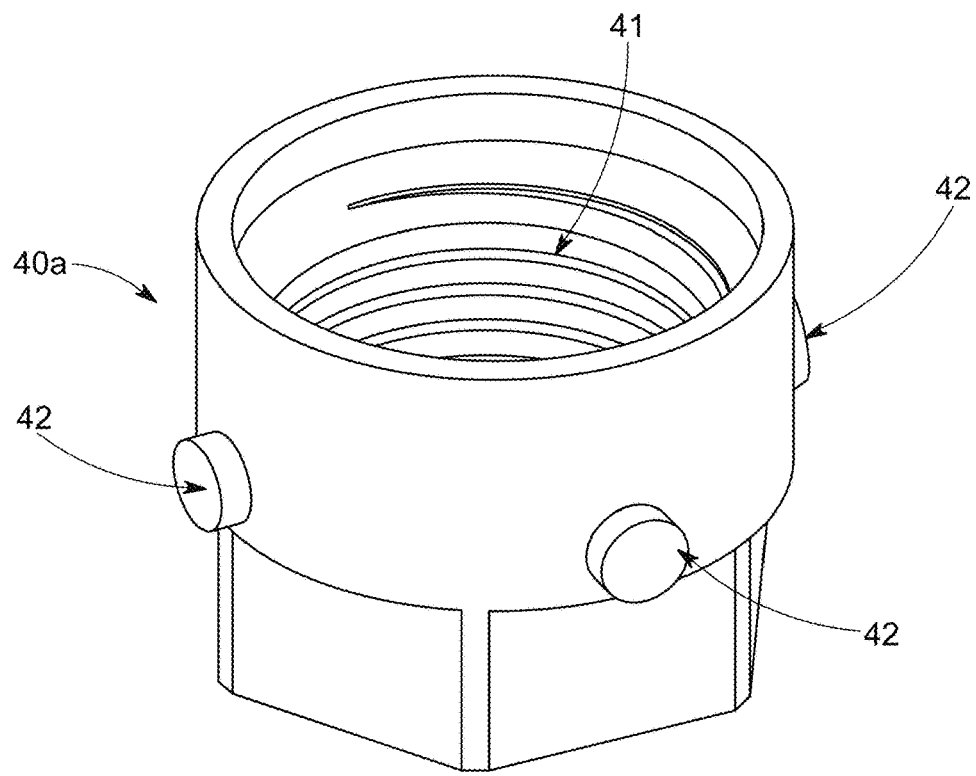
Figure 29:
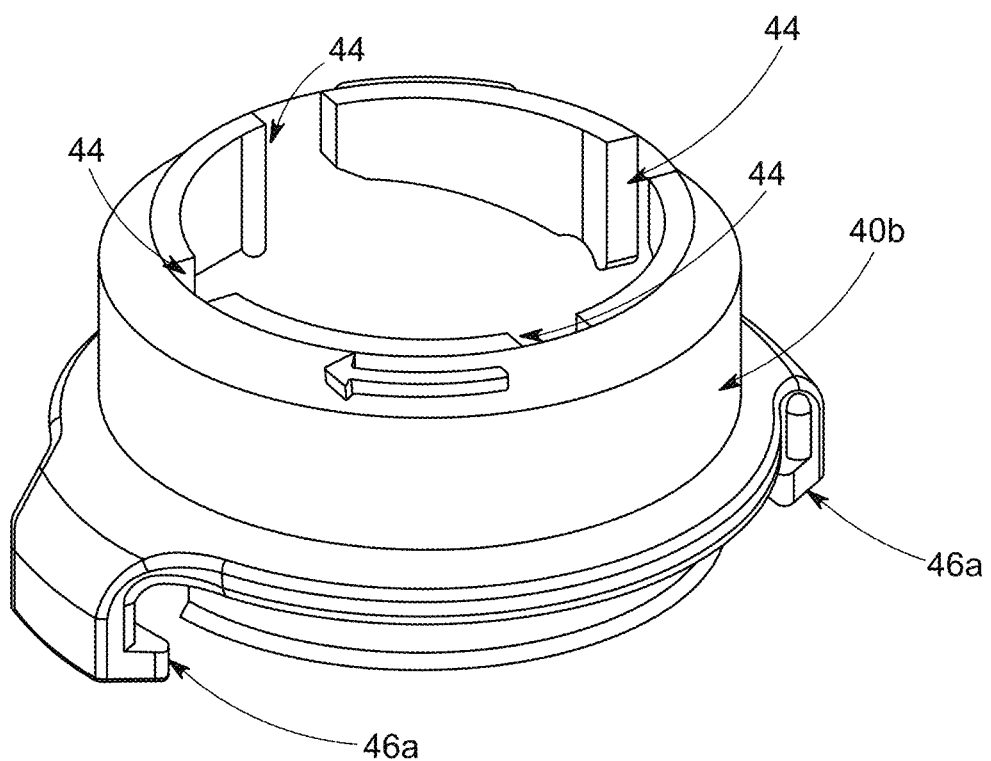
Figure 30:
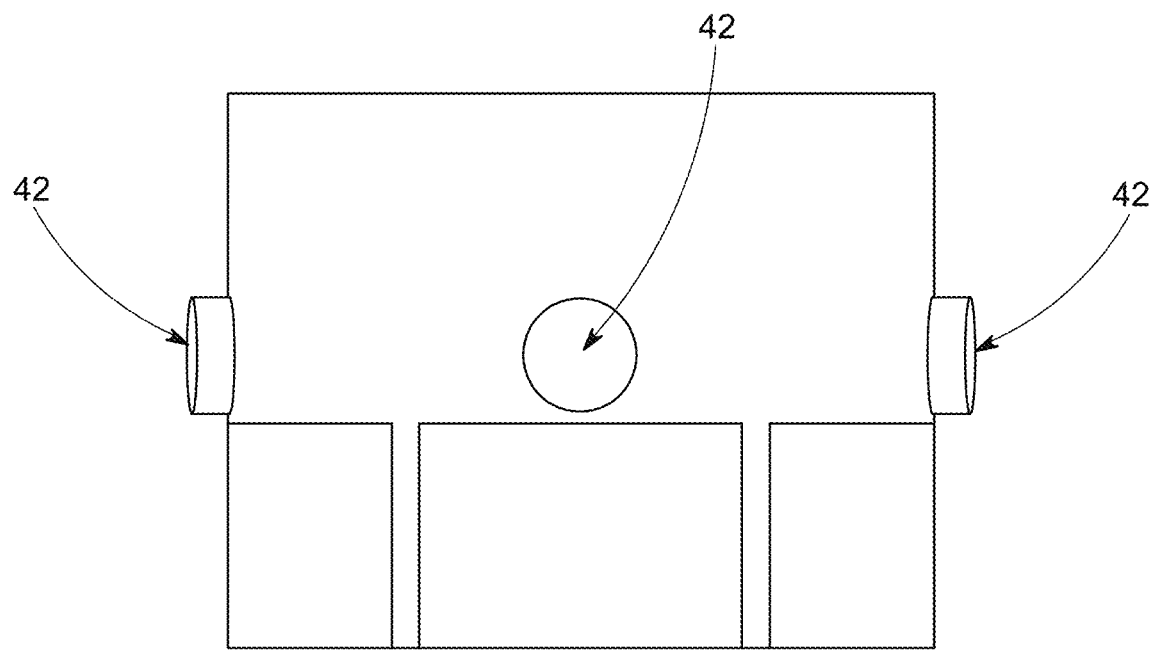
Figure 31:
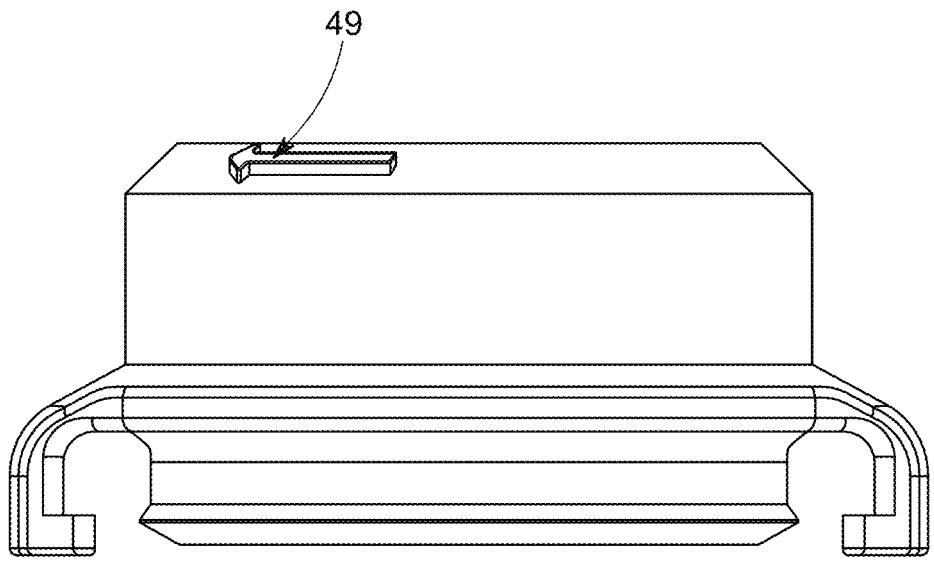
Figure 32:
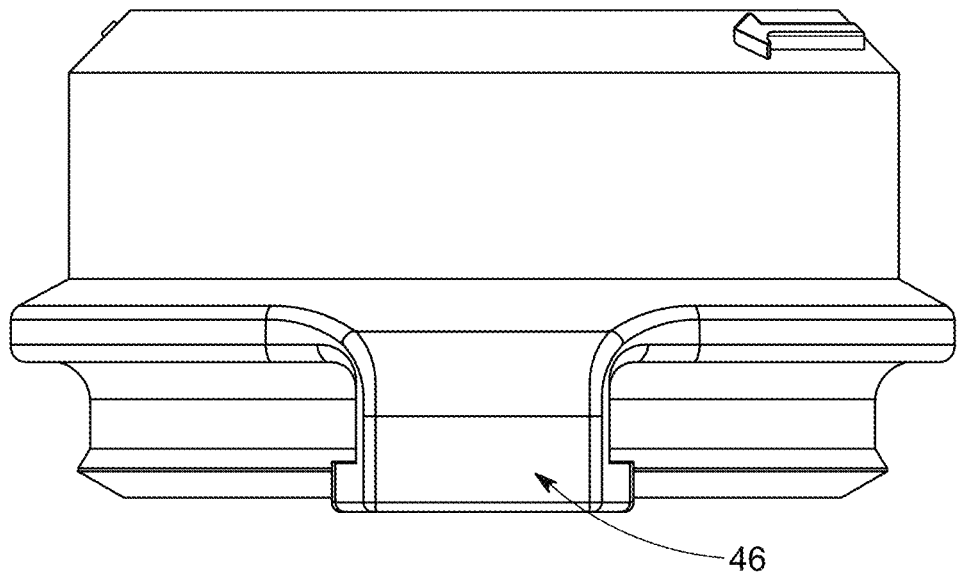
Figure 33:
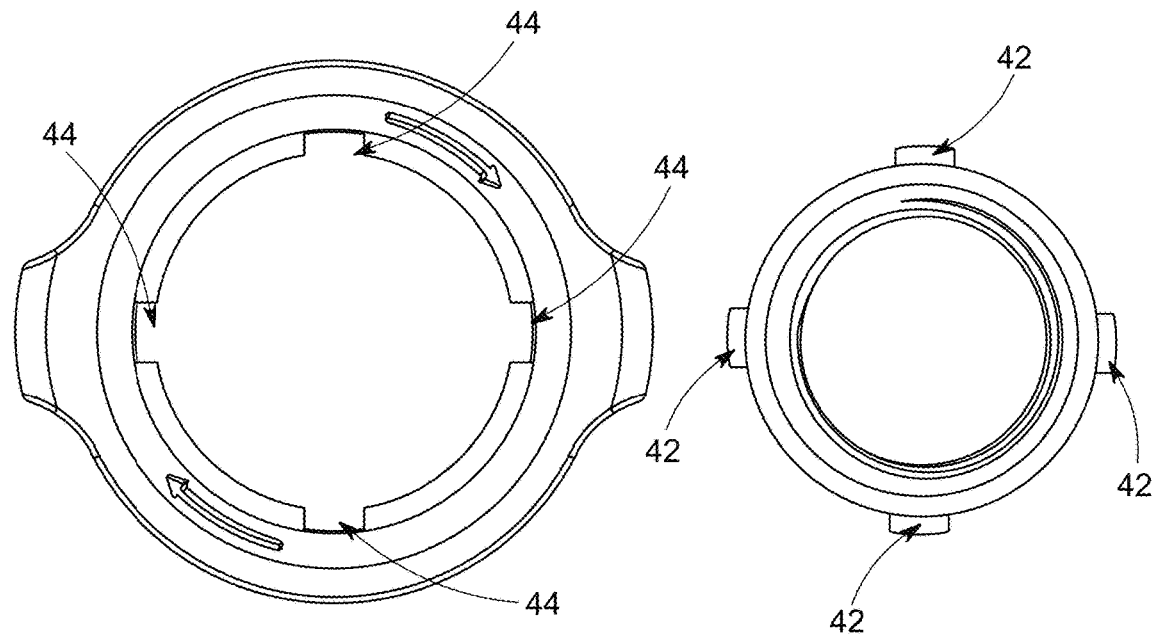
Figure 34:
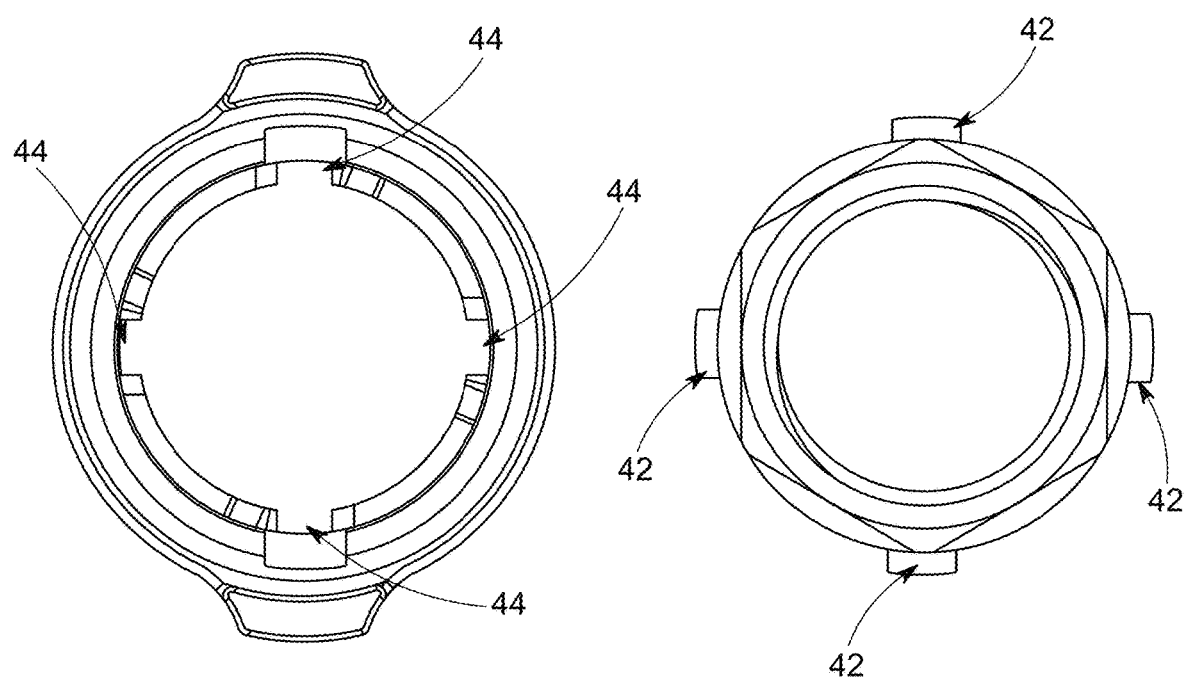
Figure 35:
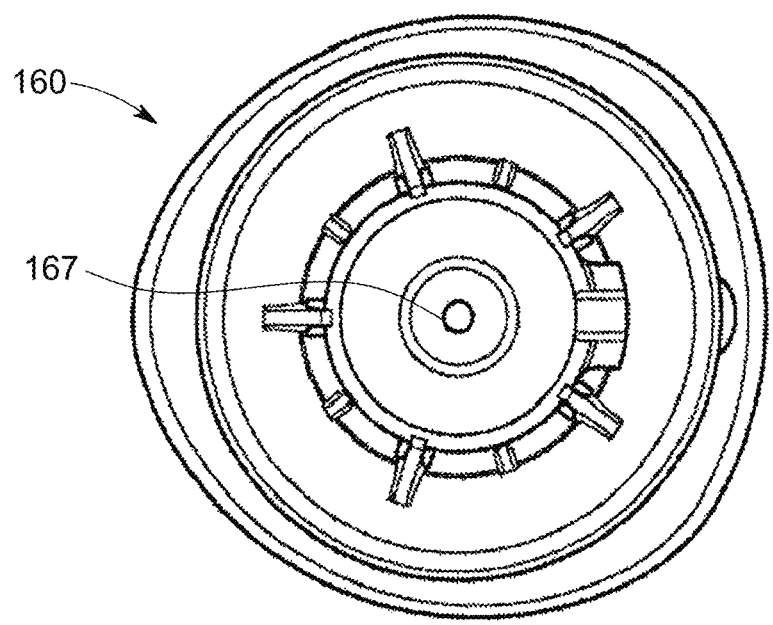
FIG. 35 illustrates a top view of a portable gas delivery system comprising a nozzle according to the present invention.
Figure 36:
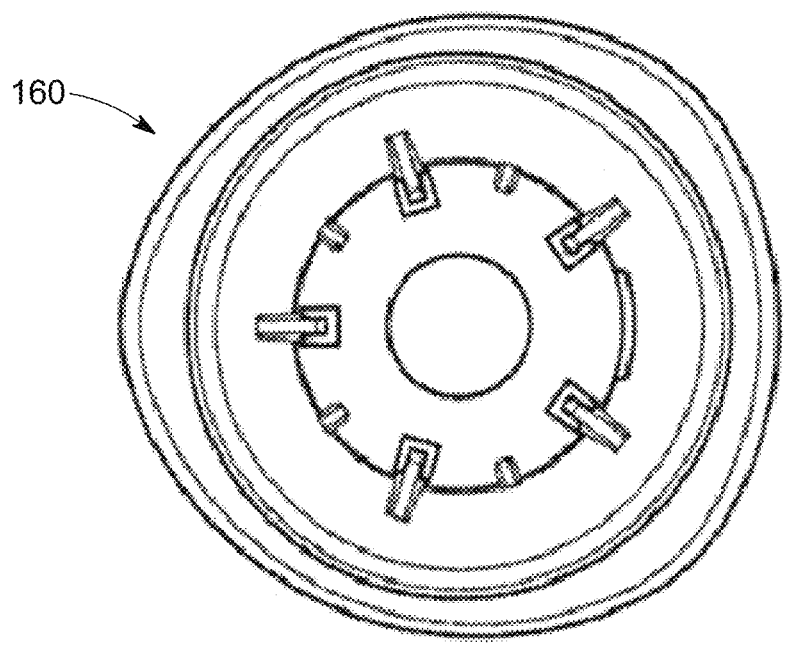
FIG. 36 illustrates a top view of a portable gas delivery system lacking a nozzle according to the present invention.
Figure 37:
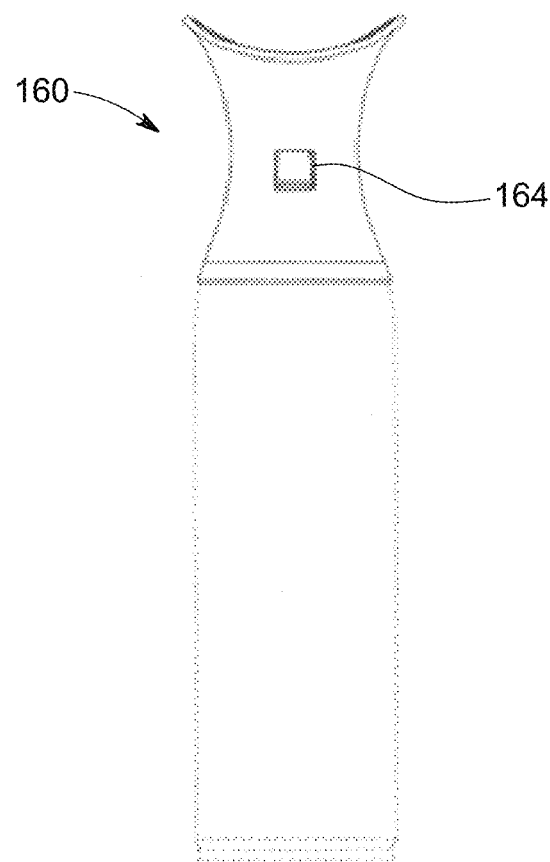
FIGS. 37 and 40 illustrate a side view of a portable gas delivery system according to the present invention.
Figure 38:
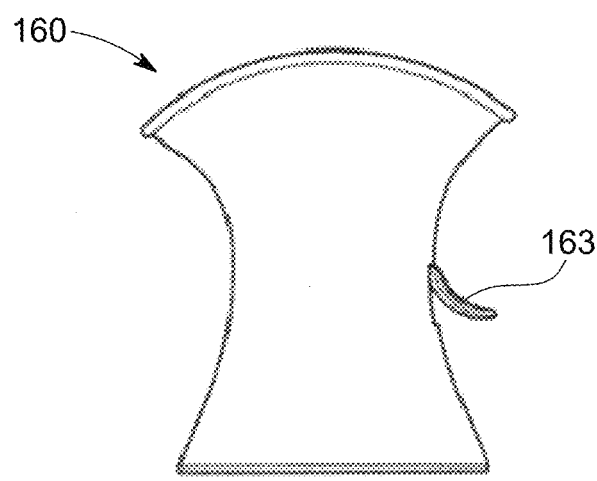
FIGS. 38 and 39 illustrate side and perspective views of a mask of the portable gas delivery system according to the present invention.
Figure 39:
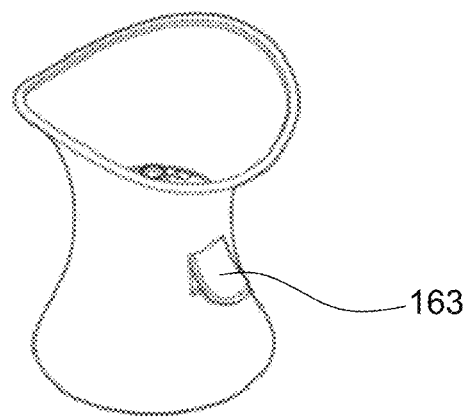
Figure 40:
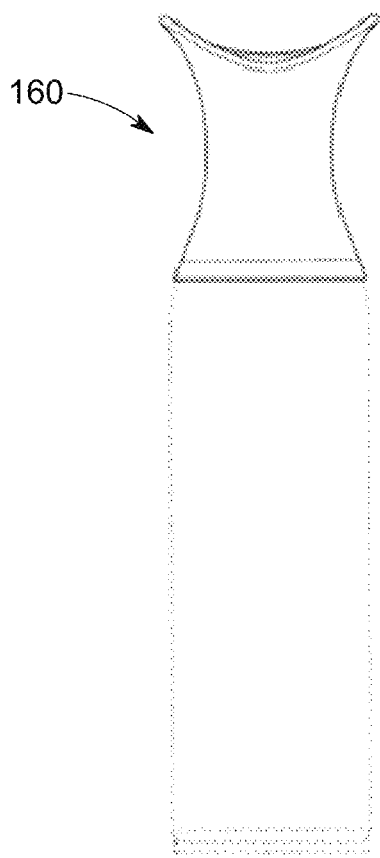
Figure 41:
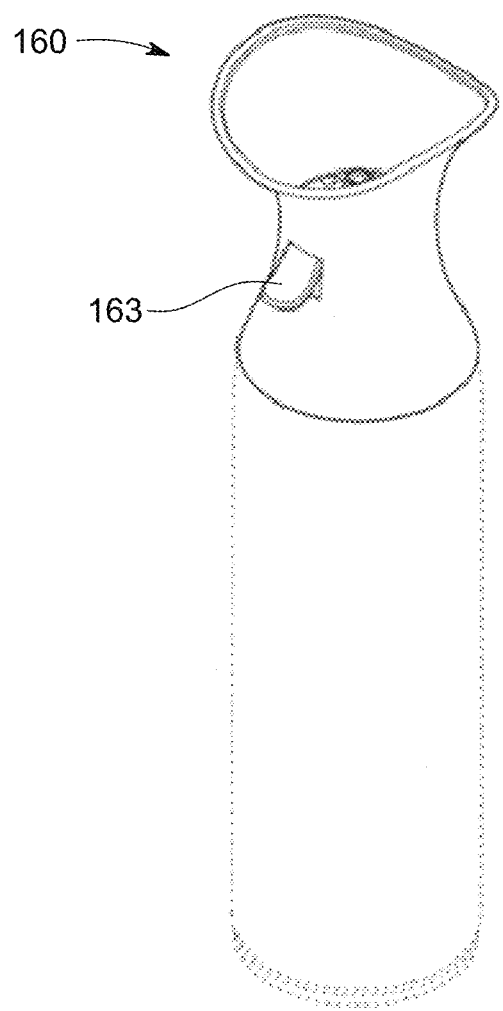
FIG. 41 illustrates a perspective view of the portable gas delivery system according to the present invention.
Figure 42:
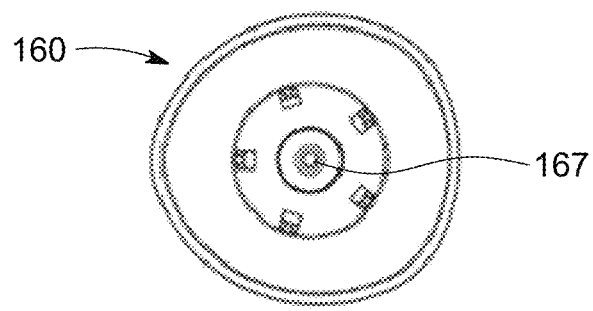
FIG. 42 illustrates a bottom view of a portable gas delivery system comprising a nozzle according to the present invention.
Figure 43:
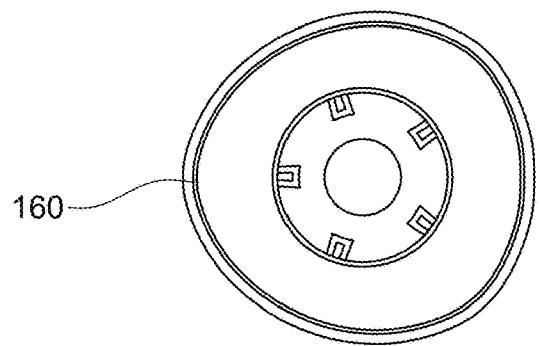
FIG. 43 illustrates a bottom view of a portable gas delivery system lacking a nozzle according to the present invention.
Figure 44:
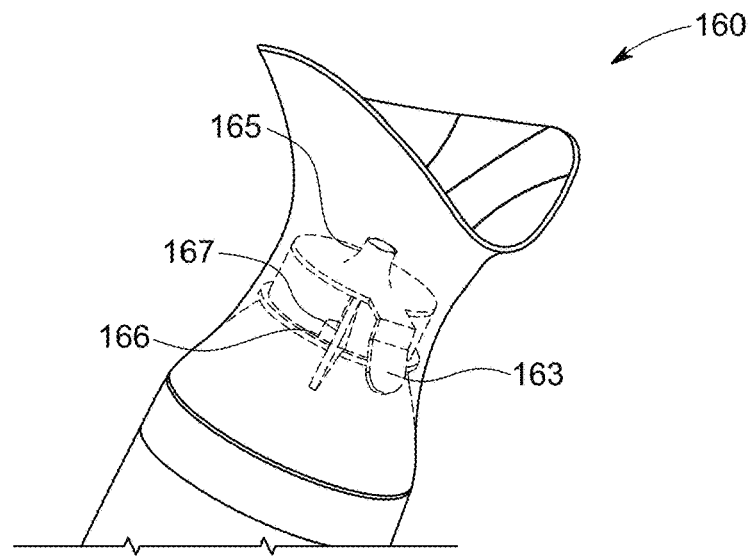
FIGS. 44-46 and 51-54 illustrate a portable gas delivery system according to the present invention.
Figure 45:
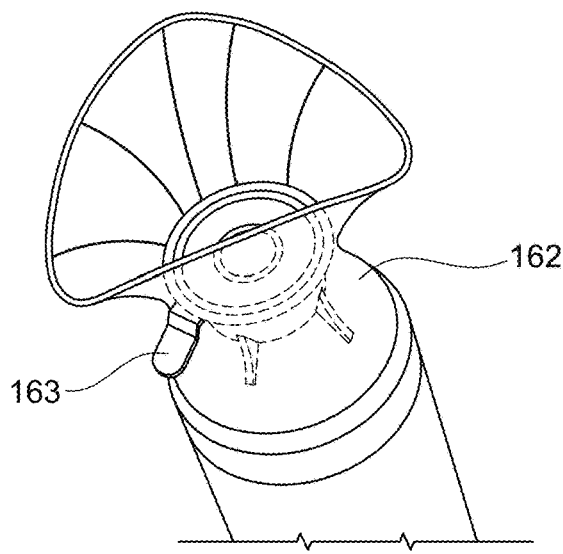
Figure 46:
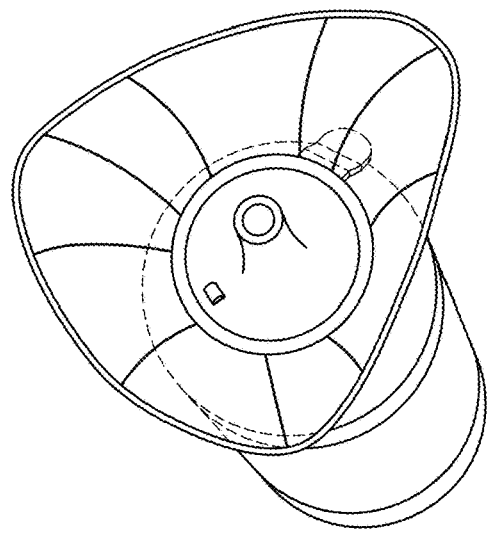
Figure 47:
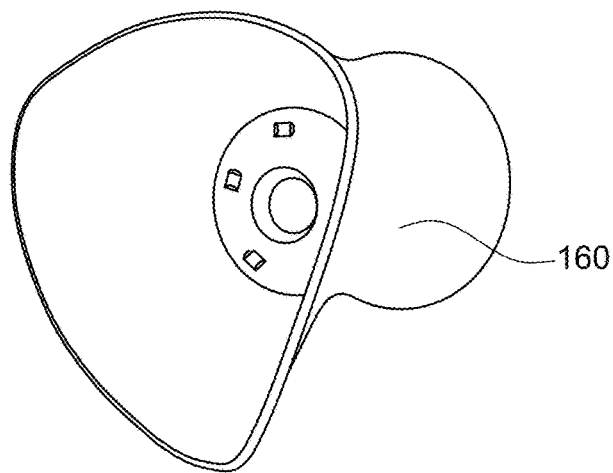
FIG. 47 illustrates a mask of a portable gas delivery system according to the present invention.
Figure 48:
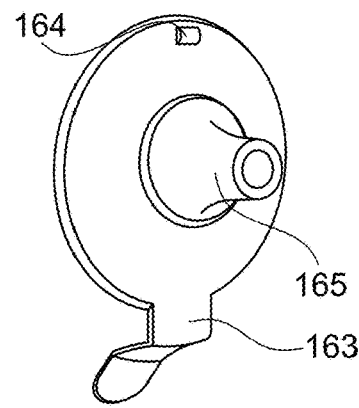
FIGS. 48-50 illustrate a nozzle and trigger of a portable gas delivery system according to the present invention.
Figure 49:
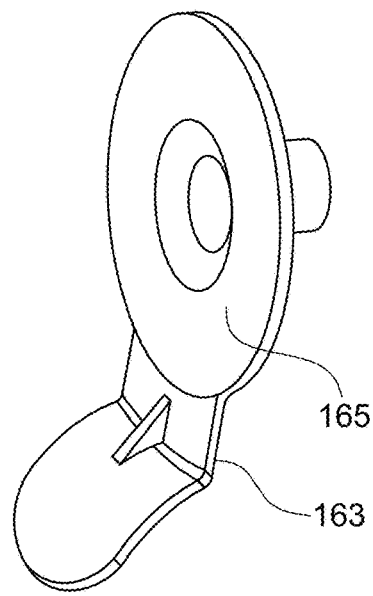
Figure 50:
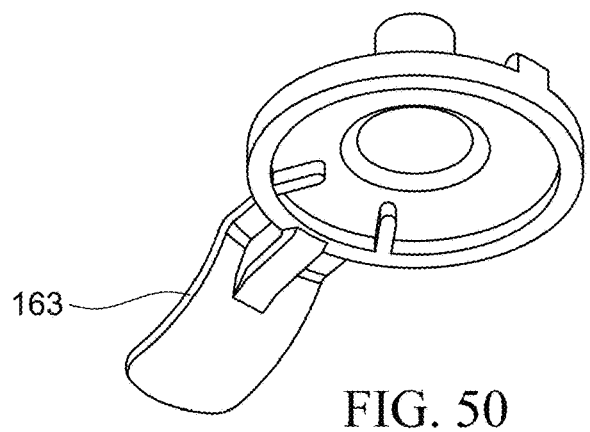
Figure 51:
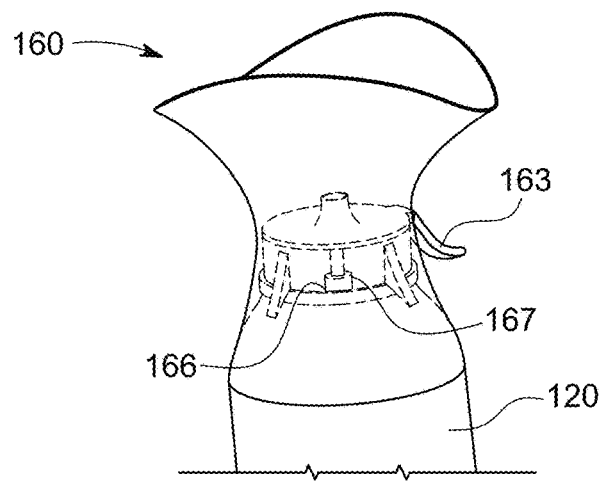
Figure 52:
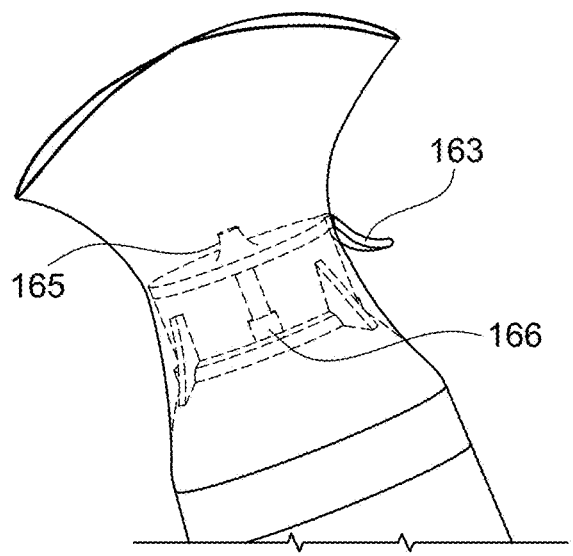
Figure 53:
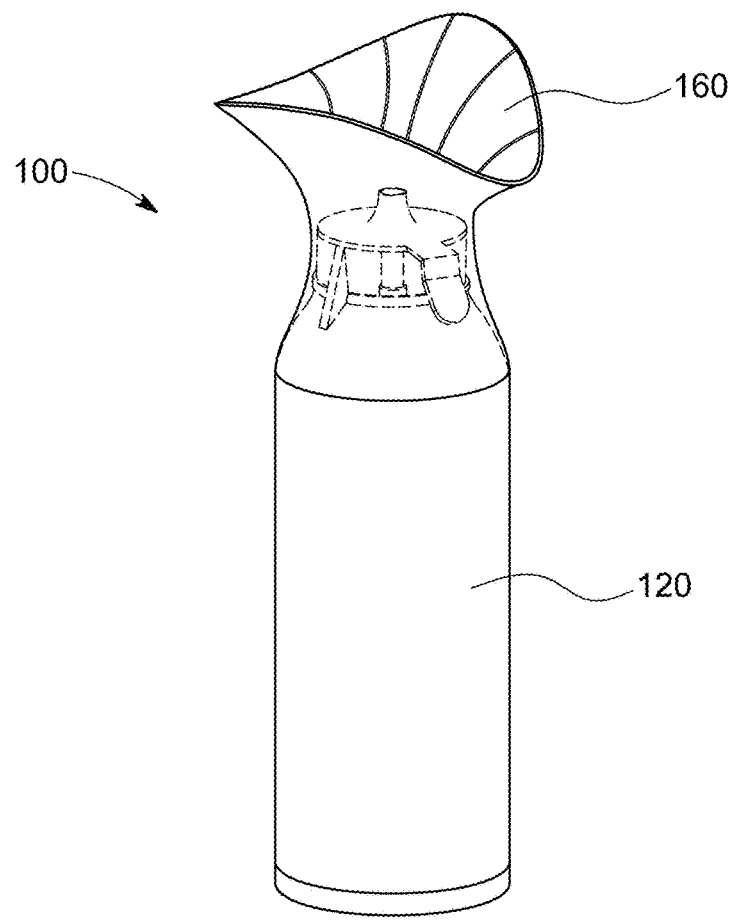
Figure 54:
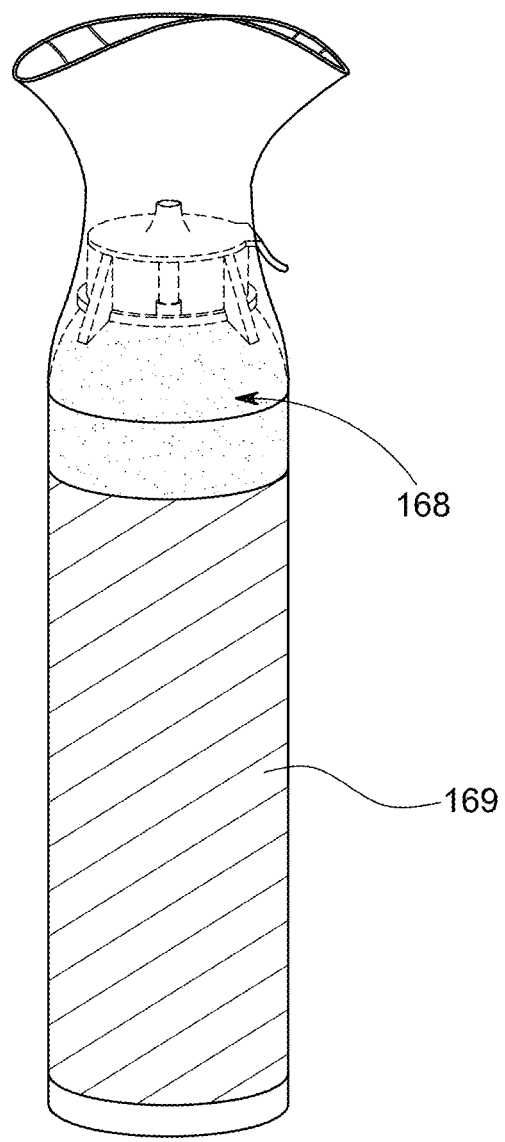

The container may comprise 100-1000 PSI medical grade oxygen and/or air at room temperature, such as 100-500 PSI, 100-250 PSI, and/or 210-240 PSI. As shown in FIGS. 4 and 5, the container 20 may comprise an aerosol-type container including a valve. The valve may comprise a valve cup 22 and a valve stem 24 or nozzle. The body of the container may comprise metal, such as steel and/or aluminum, having a minimum wall thickness of 0.008 inch. The valve may comprise metal and/or plastic. The container and/or valve may be integral with the outer portion 40B of the adapter 40.

The container may comprise an absorbent to adsorb the gas and increase the storage and/or working capacity of the gas within the capacity of the container. The absorbent may comprise a gas to be adsorbed into a sorbent material comprising a compatible adsorbent material at a superatmospheric pressure, i.e., a positive gauge pressure. The sorbent material may comprise a material having sorptive affinity for the gas to be stored in and dispensed from the container. The sorbent material may comprise activated carbon, zeolites, alumina, silica, molecular sieve materials, metal organic frameworks, and other inorganic and organic sorbents. Carbon material may be prepared from carbon sources including natural carbonaceous sources, such as peat, wood, coal, nutshell (such as coconut), petroleum coke, bone, and bamboo shoot, drupe stones and various seeds; and synthetic sources, such as poly(acrylonitrile) or phenol-formaldehyde. The activated carbon may comprise coconut activated carbon having an iodine number of at least 1050 mg/g, an ash up to 4 wt %, a moisture up to 5 wt %, an apparent density of at least 0.48 g/mL, a hardness number of at least 95, a 12 US Mesh (1.70 mm) of up to 5 wt %, and a less than 40 US Mesh (0.425 mm) (PAN) of up to 4 wt %.

The carbon may be activated to develop an intricate network of pores and surface area sufficient for adsorption. The pores may have various sizes ranging from macroporous to microporous to sub-microporous dimensions of molecular-sized entities. The larger transport pores may provide access to the smaller pores in which most of the adsorption of gas may take place. Carbon activation may be conducted with gaseous activation using steam, carbon dioxide or other gases at elevated temperatures, or chemical activation using, for example, zinc chloride or phosphoric acid. Other activation processes may be used to achieve the pore structure and surface area that provides an extensive physical adsorption property and a high volume of adsorbing porosity. The activated carbon may comprise powdered, granular and/or pelleted products. The activated carbon may also be in the form of a cloth, felt or fabric.

The activated carbon may comprise a relatively high prevalence of micropores and a low enthalpy of adsorption to enable a substantially maximum gas delivery. The micropores may have a size up to 50 nanometers, such as 0.5-50 nanometers, 0.5-2.5 nanometers, and/or 1-2 nanometers, for example, and the macropores may have a size greater than 50 nanometers. The enthalpy of adsorption may be less than about 25 kJ/mole of adsorbate. In other words, a carbon with a high capacity uptake for the gas and a low retention (or heel) on discharge may provide for the maximum gas volume delivery. For a high uptake, the activated carbon may have a high concentration of micropores. For a low retention, carbons with a low enthalpy of adsorption (for the particular gas) may be used. Without wishing to be bound to any particular theory, the activated carbon may facilitate condensation and/or immobilization of gases resulting in increased gas storage and delivery capacity relative to a non-absorbed-filled container having the same liquid volume despite the volume lost to the absorbent.

Without wishing to be bound to any particular theory, the absorbent may increase the gas storage capacity relative to conventional portable gas delivery system. For example, the present invention may improve the storage capacity of a gas, such as oxygen, by at least three times at constant pressure and temperature conditions relative to conventional portable gas delivery systems. The absorbent may increase the gas capacity of the container by up to 10 times, such as 1.5-10 times, 1.5-5 times, 5-10 times, 2 times, 3 times, or 4 times relative to the same portable gas delivery system lacking the absorbent. The ratio of gas volume of gas under pressure at room temperature of a container comprising the absorbent relative to a container lacking the absorbent may be greater than 1:1, 1.5:1 to 10:1, such as 2:1, 3:1, 4:1, and greater than 10:1. For example, the container comprising the absorbent may have a liquid gas volume of 0.65 L and a gas volume of 20 L of gas under pressure at room temperature. The container may store 1-60 L of 95% oxygen and operate from 100-500 PSI. More specifically, the container may store 15-30 L of 95% oxygen and operate from 120-240 PSI.

The container may be at least partially filled with the absorbent, such as activated carbon, for example. The container may comprise a first portion and a second portion. The first portion may be adjacent and/or proximate to the outlet of the container. The first portion may be adjacent and/or proximate to the valve of the container. The first portion may be intermediate the outlet of the container and the second portion. The first portion may comprise a filter, such as a foam filter, and the second portion may comprise the absorbent. The filter may completely fill (at least 95% of the total volume), substantially fill (at least 50% of the total volume), or at least partially fill (greater than 0% of the total volume) the first portion. The absorbent may completely fill (at least 95% of the total volume), substantially fill (at least 50% of the total volume), or at least partially fill (greater than 0% of the total volume) the second portion. When the container lacks a filter, the absorbent may completely fill (at least 95% of the total volume), substantially fill (at least 50% of the total volume), or at least partially fill (greater than 0% of the total volume) the container. The container may have a ratio of the first portion to the second portion of 1:1 to 1:100, such as 1:5 to 1:25 and 1:10. The first portion may comprise up to 25 volume % of the capacity of the container and the second portion may comprise at least 50 volume % of the capacity of the container. For example, the first portion may comprise up to 10 volume % and the second portion may comprise at least 90 volume %. The container may comprise 1-1000 g of absorbent, such as 100-500 g, 200-400 g, and/or 500-1000 g. For example, the container may comprise 330 g absorbent and 210 PSI oxygen at room temperature. The container may comprises an absorbent weight (g) to volume (mL) ratio of the absorbent to oxygen from 100:1 to 1:100. For example, the container may comprise 330 g absorbent and 0.65 L volume and have a ratio of 1:2.

The regulator may comprise a maximum inlet pressure up to 3000 PSI and an outlet pressure up to 1000 PSI. The regulator may comprise a low-pressure regulator having an outlet pressure 0-1000 PSI, greater than 0 to 1000 PSI, up to 500 PSI, 0-500 PSI, greater than 0 to 500 PSI, up to 250 PSI, 0-250 PSI, greater than 0-250 PSI, up to 200 PSI, 0-200 PSI, greater than 0-200 PSI. The low pressure regulator may provide low positive pressure and absolute pressure. The regulator may comprise a single stage regulator and/or a two stage regulator. The regulator may provide a constant flow rate and/or a variable flow rate. The flow rate may comprise up to 25 liters per minute, such as up to 10 liters per minute. For example, the regulator may provide a constant flow rate of up to 0.5 liters per minute, 1 liters per minute, 2 liters per minute, and 3 liters per minute. The regulator may have a weight less than 10 pounds, less than 5 pounds, less than 2 pounds, less than 1 pound, and/or less than 0.5 pounds, such as 120 grams. The regulator may have a minimum width of at least 1 inch, a maximum width of less than 2.5 inches, and a maximum height of less than 2.5 inches. The regulator may comprise a micron filter to filter the absorbent and/or particulates from the gas, such as a 5 micron filter, for example. The regulator may comprise a reusable regulator configured for use with more than one gas containers. The regulator may comprise steel, brass, nickel, and/or aluminum. Referring to FIGS. 9-14, the regulator 30 may comprise or lack a pressure gauge 34 to indicate the amount of gas in the container. The pressure gauge may indicate the pressure, volume, and/or percentage of useable gas in the container, such as "full", 50% or %[1], and "empty", for example. The system may be configured to provide usable gas at pressures from less than 500 PSI such that 500 PSI is "full", 250 PSI is ½, and 0 PSI is "empty".

The regulator 30 may comprise an inlet 33 and an outlet 31. The inlet 33 may comprise a threaded male inlet 36 and the outlet 31 may comprise a threaded male outlet and/or a barbed male outlet 32. The inlet 36 may comprise a male port configured to couple and engage with the valve stem of the container to create an airtight seal. For example, the inlet 36 may comprise a C-10 (18⅝ inch UNF) male threading. The inlet may not directly couple to the container and/or valve. For example, the container and/or valve may lack female threads to engage the threaded male inlet of the regulator. The inlet 33 may couple to the valve stem of the container. The inlet 33 may sealingly engage the valve stem of the container when the regulator 30 is coupled to the container 20. The regulator and/or inlet may be integrated with the inner portion of the adapter. The regulator may comprise a barbed-end to engage and/or securely couple the tube or cannula to the regulator when the tube or cannula is used.

Referring to FIGS. 15-34, the adapter 40 may comprise a two-piece connector to sealingly couple the regulator 30 to the container 20. The adapter 40 may comprise an inner portion 40A and an outer portion 40B. The inner portion 40A may couple to the regulator 30 and the outer portion 40B may couple to the container 20. For example, the inner portion 40A may comprise female threads 41 to threadingly engage the threaded male inlet 36 of the regulator 30. The outer portion 40B may comprise one or more tabs 46, such as 2, 3, 4, 5, or more than 5 tabs, to engage the valve cup 22 of the container 20. The tabs 42 may be orthogonal in direction to the threads 41 on the inner surface of the outer portion 40B. The inner portion 40A may comprise ⅝ inch 18 UNF female threading or a CGA C-10 connection) on the inner surface thereof. The outer portion 40B and container 20 may be pushed together until the one or more tabs 46A engage the valve cup 22 of the container 20. The one or more tabs 46A may generate an audible click when the outer portion 40B engages the valve cup 22.

The regulator 30 may be coupled to the container 20 when the inner portion 40A engages and couples to the outer portion 40B. The inner portion 40A may comprise at least one tab 42, such as 1, 2, 3, 4, 5, or more than 5 tabs, on the outer surface thereof and the outer portion 40B may comprise at least one complimentary slot 44 on the inner surface thereof. The at least one tab 42 may be aligned with the at least one complimentary slot 44 and turned in a first direction up to 90° and/or greater than 90° to slidingly engage the at least one complimentary slot 44 to cause gas to flow from the container 20. The at least one tab 42 may be turned up to 90° in an opposite direction to disengage the outer portion 408 from the inner portion 40A and/or decrease or stop gas flowing from the container 20. For example, a user may insert the tabs 42 into the complimentary slots 44 and turn the regulator 30 and/or inner portion 40A relative to the container 20 and/or outer portion 40B to begin flow of the gas from the container 20. This may allow for a disposable aerosol-type container to be used with a reusable (and possibly more expensive) regulator. When the inner portion 40A comprises more than one tab 42, the shape and/or location of the more than one tab 42 may be different to engage the outer portion 40B in only one way. The outer portion and inner portion may independently comprise glass, metal, and/or plastic.

Referring to FIGS. 35-54, a portable gas delivery system according to the present invention may generally comprise a mask 160 removably coupled to a container 120 including an absorbent 169 and a gas at least partially absorbed on the absorbent 169. The container 120 may comprise a leak-tight gas vessel. The mask 160 may comprise a face piece 160, a trigger 163, and an external filter 166. The mask 160 may comprise clips or hooks 162 to couple to the ridge of the container 22 to secure the mask 160 to the container 120.

The trigger 163 may extend through a notch 164 in the side of the face piece 160. The trigger 163 may fit into a complimentary indent of the mask 160 to secure the trigger 163 in place and/or reduce undesirable motion. The trigger 163 may include elevated ribs/features/protrusions on the under-side of the trigger body to increase mechanical advantage and/or to aid in the function of the trigger assembly. The trigger 163 may be integral with the nozzle 165 of the mask 160. The trigger 163 may be coupled to the external filter 166. The external filter 166 may be configured to be removeably coupled directly to the top of the valve 167 of the container 120. The valve 167 may comprise the external filter 166. For example, the filter 166 may comprise an syringe filter, such as a 25 mm diameter and 0.22 micrometer polyethersulfone syringe filter. The filter 166 may comprise nylon, polyvinylidene fluoride, polytetrafluoroethylene, and other polymers or materials suitable for filtering. The filter 166 may remove any absorbent particulates from the absorbent 169 that entered into the gas stream.

The container 120 may comprise an internal filter 168. The internal filter 168 may be positioned between the valve 167 and the absorbent 169. The foam insert may be compressed to configure to the internal space of the container 120. The internal filter 168 may comprise a foam insert comprising a polyurethane foam having a density from 0.8-0.9 lb/ft3. The foam insert may have a generally cylindrical shape and a diameter of 2.5 inches and a height of 1.5 inches The foam insert may comprise an open cell foam or a closed cell foam. The foam insert may comprise high density polyurethane and/or low density polyurethane.

A method of using the portable gas delivery system may generally comprise pressing the mask to the face (trigger facing outward, top of mask just below nose), pressing the trigger, and inhaling the gas. Depressing the trigger may actuate the valve and create a pressure differential between the outside of the container and the inside of the container. This pressure difference may cause oxygen to desorb from the carbon absorbent inside the container and flow through the internal filter (e.g., the foam insert positioned inside the container), the valve, and the external filter. The internal filter may comprise a die-cut foam insert made from polyurethane. The internal filter may comprise a cylindrical shape and have a 2.5 inch diameter and a 1.5 inch height. The internal filter may be configured to fill the void in the container between the carbon adsorbent and the top of the container. The internal filter may mitigate movement of the carbon absorbent, and therefore mitigate dust and particulate generation. The internal filter may filter the oxygen gas flowing through it before passing through the valve.

A method of making a portable oxygen device according to the present invention could generally involve 3D printing, machining, injection molding, or another process by which polymers and/or metals are precisely shaped.

The following aspects are disclosed in this application:

1. A portable gas delivery system for dispensing medical grade gas to a patient, the system comprising: a portable, low pressure gas container comprising an outlet, a pressurized medical grade gas up to 250 PSI, an internal liquid volume up to 1 L, an internal gas volume up to 15 L at 200-250 PSI and room temperature, and a burst pressure less than 500 PSI at room temperature; a low pressure regulator comprising an inlet and an outlet, and in fluid communication with the container to provide the gas at an adjustable volumetric flow rate from 0-10 L/min and having an inlet pressure up to 250 PSI at room temperature; and a two piece adapter comprising an inner portion removably coupled to and slidably engaged with an outer portion to control a flow of gas between the container and regulator, wherein the inner portion is threadingly engaged to the inlet of the regulator and the outer portion is coupled to the container; and a mask to receive at least one of the patient's mouth and nose removably coupled to the outlet of the regulator, and wherein the container and the regulator each have a weight less than 0.5 lbs, and wherein the system is in an open position when the inner portion of the adapter is in a first position and the system is in a closed position when the inner portion of the adapter is in a second position.

2. The system of aspect 1, wherein the gas container comprises a single-use and non-refillable gas container having an internal liquid volume up to 0.65 L.

3. The system of aspects 1 or 2, wherein the gas container comprises an absorbent and the medical grade gas is pressurized and at least partially absorbed on the absorbent.

4. system of aspects 1-3, wherein the absorbent comprises activated carbon and the medical grade gas is oxygen.

5. The system of aspects 1-4, wherein the regulator provides the gas at an adjustable volumetric flow rate of 0.5-3 L/min and an inlet pressure of 50 PSI at room temperature.

6. The system of aspects 1-5, wherein the container and regulator provide a constant flow rate for single-use at room temperature of up to 3 gaseous liters per minute for a duration up to 3.3 minutes.

7. The system of aspects 1-6, wherein the container comprise an aerosol-type container comprising a valve cup and a valve stem, and wherein the inlet of the regulator sealingly engages the valve stem of the container when the outer portion of the adapter is snap fitted to the valve cup, and wherein the container has a burst pressure up to 400 PSI.

8. The system of aspects 1-7, wherein the inner portion of the adapter comprises at least one tab on the outer surface thereof and the outer portion comprises at least one complimentary slot on the inner surface thereof.

9. The system of aspects 1-8, wherein the at least one tab slidingly engages the at least one complimentary slot to cause gas to flow from the container when turned up to 90° in a first direction.

10. The system of aspects 1-9, wherein the at least one tab slidingly engages the at least one complimentary slot to reduce the flow of gas from the container when turned up to −90° in a second direction.

11. The system of aspects 1-10, wherein the regulator is not a single-use regulator.

12. The system of aspects 1-11 comprising an integrated regulator, adapter, and mask.

13. The system of aspects 1-12 comprising an integrated regulator and inner portion of the adapter, and an integrated container and outer portion of the adapter.

14. The system of aspects 1-13 comprising an integrated inner portion and outer portion of the adapter.

15. A handheld, portable oxygen delivery system for dispensing medical grade oxygen to a non-human animal comprising the portable oxygen system of aspects 1-14.

16. The system of aspects 1-15, wherein the gas container comprise a single-use and non-refillable gas container and the regulator is not a single-use regulator.

17. The system of aspects 1-16, wherein the container and regulator provide a constant flow rate for single-use at room temperature of up to 3 gaseous liters per minute for a duration up to 3.3 minutes.

18. The system of aspects 1-17, wherein the container comprise an aerosol-type container comprising a valve cup and a valve stem, and wherein the regulator sealingly engages the valve stem of the container when the outer portion of the adapter is snap fitted to the valve cup.

19. The system of aspects 1-18, wherein the inner portion of the adapter comprises at least one tab on the outer surface thereof and the outer portion comprises at least one complimentary slot on the inner surface thereof.

20. The system of aspects 1-19, wherein the at least one tab slidingly engages the at least one complimentary slot to cause gas to flow from the container when turned up to 90° in a first direction from the first position to the second position and reduces the flow of gas from the container when turned in an opposite direction from the second position.

EXAMPLES

The present invention may be better understood when read in conjunction with the following representative examples. The following examples are included for purposes of illustration and not limitation.

Example 1: Oxygen Therapy for Respiratory-Diseased Persons

The portable gas delivery system may be used to provide reliable flow of oxygen gas for oxygen therapy. The adapter may be coupled to an aerosol-type container and a regulator. A nasal cannula and oxygen mask may be coupled to the barbed-end of the regulator and used to deliver oxygen from the container via the adapter and regulator, to a patient. The container may comprise a disposable container and the regulator may comprise a reusable regulator to allow the patient to use the same regulator with more than one oxygen supply containers.

Example 2: Oxygen Treatment for Veterinary Use

The portable gas delivery system may be used to provide reliable flow of oxygen, air, or another breathable gas to an animal (e.g., a dog or a cat) that may benefit from supplemental oxygen during treatment or while in transit. Currently, supplemental oxygen may be used for animals in primary and secondary care facilities by veterinarians, as well as in transit and in the home by pet-owners. The portable gas delivery system having a disposable container and reusable regulator may allow for more convenient and safe oxygen therapy for pets.

Example 3: Nitrous Oxide Treatment

The portable gas delivery system may be used to provide reliable flow of nitrous oxide gas to a human or animal for anesthetic purposes. Nitrous oxide is a well-known medical gas used for anesthetic on both humans and animals. In certain cases, it may be desirable to access a portable supply of nitrous oxide gas, for example, in battlefield situations, while maintaining accurate flow rate and dosing. The deliverable gas may comprise a mixture of gases, such as nitrous oxide and oxygen, depending on the application.

Example 4: Charging the Container with Gas

Activated Carbon OLC 12×40 may be obtained from Calgon Carbon, Pittsburgh, Pa. The activated carbon is characterized by an average relative humidity of facility of greater than 40%, such as greater than 25%, an ash less than 4.0 weight percent, a moisture less than 5.0 weight percent, and a hardness greater than 95. A foam, such as 3215 SM foam, may be obtained from Innocor foam technologies, Newburyport, Mass. The foam may have a diameter of 2.5 inches and a thickness of 1.5 inches. 1-1000 grams of the activated carbon, such as about 330 grams, may be poured from an auger into the gas container for 1-1000 seconds, such as about 10 seconds. Next, the foam may be inserted into the container onto the surface of the activated carbon to fill any remaining volume in the container. A valve assembly may be crimped to the top of the container. Vacuum may be applied to the container prior to filling with the gas to be stored therein. The vacuum pressure may be 8-10 lb, such as 8 lb, for a duration of 0.1-5 seconds, such as 1 second.

The gas to be stored in the container may be charged to the container at a pressure supply range of 100-1000 PSI, such as 510 PSI, for a fill time of 0.1-100 seconds, such as 6 seconds, a fill pressure of 160-240 PSI (at 70° F.), such as 220 PSI, a settling pressure of 140-180 PSI, such as 160 PSI, and a fill temperature of 50-90° F., such as 70° F., and a maximum temperature swing of 40° F.

The gas to be stored in the container may be charged to the container at a carbon temperature of −40° F., an oxygen temperature of 70° F., an oxygen supply pressure of 100-1000 PSI at room temperature, such as 510 PSI for a fill time of 0.1-100 seconds, such as 4 seconds, a fill pressure of 160-240 PSI (at 70° F.), such as 170 PSI, a settling pressure of 140-180 PSI, such as 180 PSI.

The oxygen may comprise liquid oxygen, which may be charged to the container at a carbon temperature of 70° F. and an oxygen temperature of −300° F., a fill time less than 1 second and a LOX dosage of 26.29 mL=0.973 mol=30 g.

Example 5: Use of the Portable Gas Delivery System

To use the portable gas delivery system, the inner portion of the adapter may be threaded onto the regulator and secured tightly. The outer portion of the adapter may be "snapped" onto the valve cap. Next, the tabs of the inner portion may be aligned with and inserted into the complementary slots of the outer portion. Then, the inner portion and/or regulator may be turned up to 90° in a clockwise direction as shown by the embossed arrow on the outer portion. The twisting motion may allow the inner portion to follow a sloped guide on the inside circumference of the outer portion causing the regulator to depress the valve stem of the aerosol-type container and dispense the gas therein. The inner portion and regulator may form an air-tight seal to direct gas flow into the inlet of the regulator and from the barbed-end outlet of the regulator.

All documents cited herein are incorporated herein by reference, but only to the extent that the incorporated material does not conflict with existing definitions, statements, or other documents set forth herein. To the extent that any meaning or definition of a term in this document conflicts with any meaning or definition of the same term in a document incorporated by reference, the meaning or definition assigned to that term in this document shall govern. The citation of any document is not to be construed as an admission that it is prior art with respect to the present invention. References: U.S. D610250, U.S. D773035, U.S. Pat. No. 7,832,395, U.S. D561331, US20050081849, U.S. Pat. No. 7,341,056, US20080041375, U.S. Pat. No. 6,494,201, WO2008064293, WO2005054742, and US20030033930.

While particular exemplary embodiments of the present invention have been illustrated and described, it would be obvious to those skilled in the art that various other changes and modifications can be made without departing from the spirit and scope of the invention. Those skilled in the art will recognize, or be able to ascertain using no more than routine experimentation, numerous equivalents to the specific devices and methods described herein, including alternatives, variants, additions, deletions, modifications and substitutions. This disclosure, including the claims, is intended to cover all such equivalents that are within the spirit and scope of this invention.

What is claimed is:

1. A portable gas delivery system for dispensing medical grade gas to a patient, the system comprising:
   a portable, low pressure gas container comprising an outlet,
   a pressurized medical grade gas 200-250 PSI, an internal liquid volume of 0.25-1 L, an internal gas volume of 0.5-15 L at 200-250 PSI and room temperature, and a burst pressure greater than 250 PSI to 500 PSI at room temperature;
   a low pressure regulator comprising an inlet and an outlet, and in fluid communication with the container to provide the gas at an adjustable volumetric flow rate from 0-10 L/min and having an inlet pressure up to 250 PSI at room temperature; and
   a two piece adapter comprising an inner portion removably coupled to and slidably engaged with an outer portion to control a flow of gas between the container and regulator,
   wherein the inner portion is threadingly engaged to the inlet of the regulator and the outer portion is coupled to the container; and
   a mask to receive at least one of the patient's mouth and nose removably coupled to the outlet of the regulator, and
   wherein the container and the regulator each have a weight less than 0.5 lbs, and
   wherein the system is in an open position when the inner portion of the adapter is in a first position and the system is in a closed position when the inner portion of the adapter is in a second position;
   wherein the inner portion of the adapter comprises at least one tab on the outer surface thereof and the outer portion comprises at least one complimentary slot on the inner surface thereof; and
   wherein the at least one tab slidingly engages the at least one complimentary slot to cause gas to flow from the container when turned about 90° in a first direction.

2. The system of claim 1, wherein the gas container comprises a single-use and non-refillable gas container having an internal liquid volume of 0.25 L-0.65 L.

3. The system of claim 1, wherein the gas container comprises an absorbent and the medical grade gas is pressurized and at least partially absorbed on the absorbent.

4. The system of claim 3, wherein the absorbent comprises activated carbon and the medical grade gas is oxygen.

5. The system of claim 1, wherein the regulator provides the gas at an adjustable volumetric flow rate of 0.5-3 L/min at operating pressure and room temperature.

6. The system of claim 1, wherein the container and regulator provide a constant flow rate for single-use at room temperature of about 3 gaseous liters per minute for a duration of about 3.3 minutes.

7. The system of claim 1, wherein the container comprises an aerosol-type container comprising a valve cup and a valve stem, and wherein the inlet of the regulator sealingly engages the valve stem of the container when the outer portion of the adapter is snap fitted to the valve cup, and wherein the container has a burst pressure greater than 250 PSI to 400 PSI.

8. The system of claim 1, wherein the at least one tab slidingly engages the at least one complimentary slot to reduce the flow of gas from the container when turned in a second direction, wherein the second direction is opposite the first direction.

9. The system of claim 1, wherein the regulator is not a single-use regulator.

10. The system of claim 1 comprising an integrated regulator and inner portion of the adapter, and an integrated container and outer portion of the adapter.

11. A handheld, portable oxygen delivery system for dispensing medical grade oxygen to a non-human animal comprising the portable oxygen system of claim 1.

12. The system of claim 11, wherein the gas container comprise a single-use and non-refillable gas container and the regulator is not a single-use regulator.

13. The system of claim 11, wherein the container and regulator provide a constant flow rate for single-use at room temperature of about 3 gaseous liters per minute for a duration of about 3.3 minutes.

14. The system of claim 13, wherein the container comprise an aerosol-type container comprising a valve cup and a valve stem, and wherein the regulator sealingly engages the valve stem of the container when the outer portion of the adapter is snap fitted to the valve cup.

15. The system of claim 11, wherein the at least one tab slidingly engages the at least one complimentary slot to cause gas to flow from the container when turned about 90° in the first direction from the first position to the second position and reduces the flow of gas from the container when turned in an opposite direction from the second position.

* * * * *